United States Patent
Liebing

(10) Patent No.: US 8,814,543 B2
(45) Date of Patent: Aug. 26, 2014

(54) CONVEYING DEVICE FOR A FLUID USING AN OSCILLATING BODY ARRANGEMENT

(75) Inventor: Reiner Liebing, Potsdam (DE)

(73) Assignee: ECP Entwicklungsgesellschaft mbH, Berlin (DE)

( * ) Notice: Subject to any disclaimer, the term of this patent is extended or adjusted under 35 U.S.C. 154(b) by 0 days.

(21) Appl. No.: 13/261,361

(22) PCT Filed: Jan. 27, 2011

(86) PCT No.: PCT/EP2011/000439
§ 371 (c)(1),
(2), (4) Date: Oct. 3, 2012

(87) PCT Pub. No.: WO2011/092034
PCT Pub. Date: Aug. 4, 2011

(65) Prior Publication Data
US 2013/0019968 A1  Jan. 24, 2013

Related U.S. Application Data

(60) Provisional application No. 61/298,581, filed on Jan. 27, 2010.

(51) Int. Cl.
*F04D 33/00* (2006.01)
*A61M 1/12* (2006.01)
*A61M 1/10* (2006.01)

(52) U.S. Cl.
CPC ............. *A61M 1/12* (2013.01); *A61M 1/101* (2013.01); *F04D 33/00* (2013.01); *A61M 1/125* (2013.01)
USPC ............................................ 417/436; 623/3.1

(58) Field of Classification Search
CPC ................................. F04D 33/00; A61M 1/12
USPC ............ 417/436; 600/16, 17, 18; 137/565.01; 623/3.1, 3.22

See application file for complete search history.

(56) References Cited

U.S. PATENT DOCUMENTS

| | | | |
|---|---|---|---|
| 2,728,298 A * | 12/1955 | Shafer | 417/343 |
| 4,063,826 A * | 12/1977 | Riepe | 417/410.1 |
| 5,820,542 A | 10/1998 | Dobak, III et al. | |
| 6,544,216 B1 | 4/2003 | Sammler et al. | |
| 6,659,740 B2 * | 12/2003 | Drevet | 417/436 |
| 6,860,713 B2 | 3/2005 | Hoover | |
| 7,393,181 B2 | 7/2008 | McBride et al. | |
| 7,874,882 B2 | 1/2011 | Sagov | |
| 7,914,436 B1 * | 3/2011 | Kung | 600/18 |
| 7,927,068 B2 | 4/2011 | McBride et al. | |
| 2006/0253193 A1 * | 11/2006 | Lichtenstein et al. | 623/3.1 |
| 2011/0034874 A1 | 2/2011 | Reitan et al. | |
| 2011/0236210 A1 | 9/2011 | McBride et al. | |
| 2011/0275884 A1 | 11/2011 | Scheckel | |
| 2011/0282128 A1 | 11/2011 | Reitan et al. | |

FOREIGN PATENT DOCUMENTS

| | | |
|---|---|---|
| DE | 103 37 804 A1 | 3/2005 |
| EP | 2 194 278 A1 | 6/2010 |

(Continued)

*Primary Examiner* — Nathan Zollinger
(74) *Attorney, Agent, or Firm* — Marshall & Melhorn, LLP

(57) ABSTRACT

The invention relates to a conveying device for conveying a fluid in a conveying direction having one or more drive bodies which can be driven in an oscillating manner by means of a drive system transversely to the conveying direction. An acceleration of the fluid is achieved by a corresponding movement in translation or by a partially pivoting movement of the drive bodies in the manner of the fin principle known from biology (e.g. aerodynamics and hydrodynamics).

19 Claims, 10 Drawing Sheets

(56) References Cited

FOREIGN PATENT DOCUMENTS

| FR | 1 218 663 A | | 5/1960 |
|----|-------------|---|--------|
| GB | 2041447 A | * | 9/1980 |
| WO | WO 98/18508 A1 | | 5/1998 |
| WO | WO 2005/003545 A1 | | 1/2005 |
| WO | WO 2006/038808 A1 | | 4/2006 |
| WO | WO 2009/157840 A1 | | 12/2009 |

* cited by examiner

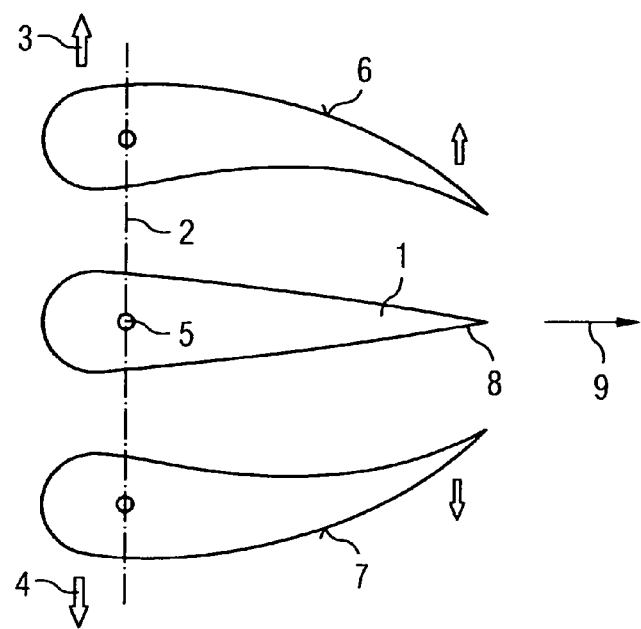
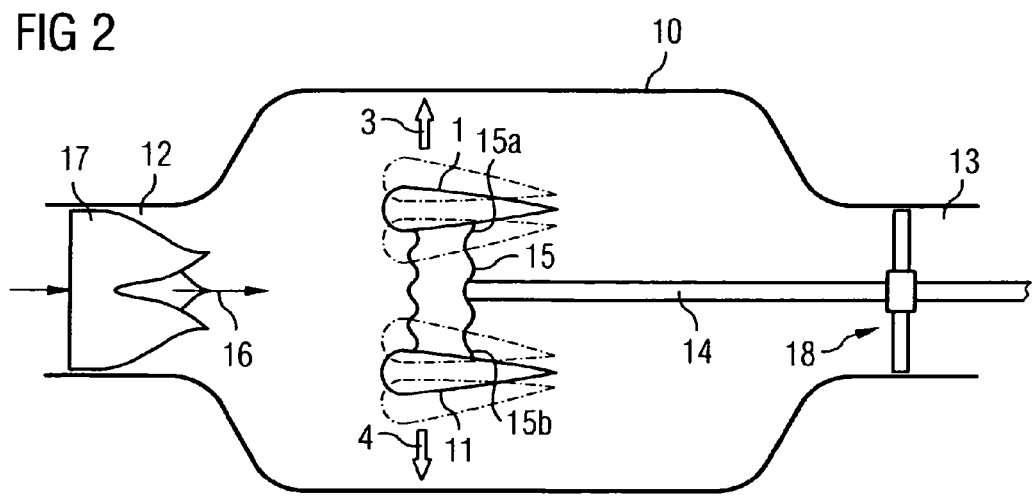

CONVEYING DEVICE FOR A FLUID USING AN OSCILLATING BODY ARRANGEMENT

BACKGROUND OF THE INVENTION

The invention is in the field of mechanical engineering and relates to conveying devices for fluids, in particular for liquids.

Such conveying devices have become known in the form of different kinds of pumps in the most varied of embodiments. Pumps are of particular interest at this point which can be manufactured in such constructions that they can be used for more sensitive fluids, in particular fluids having macromolecules. A specific group among such pumps is represented by the fluid pumps which can be used for medical application purposes and which can be manufactured in small constructions. Such pumps can also be used in micro constructions, for example, for conveying the body's own fluids, or biocompatible fluids, for example as heart pumps for conveying blood.

In the conveying of such sensitive fluids such as blood which have large and sensitive molecules, for example, which satisfy biological functions and which therefore also may not be damaged at the microscopic level, care must be taken that the mechanical effect on the fluid by pressure maxima, shear forces and accelerations is limited as much as possible.

Axial flow pumps have in particular become known in this connection, for example, for the conveying of blood which have a rotor which rotates about a longitudinal axis, which has impeller blades and which continuously conveys blood in the axial direction.

Since a specific problem for the use of such pumps in the inside of the body comprises the fact of providing them, on the one hand, with sufficient conveying capacity, and, on the other hand, however, of configuring the construction size so that they can be introduced through a blood vessel, some of the challenges for such pumps comprise the fact of configuring them from a construction aspect so that they are radially compressible and expandable again for operation in the body.

A compressible rotor of this kind is known, for example, from U.S. Pat. No. 6,860,713. Another rotor is known from U.S. Pat. No. 7,393,181 B2. In the known solutions, the rotors are compressible and expandable either due to the elasticity and deformability of the material or on the basis of mechanically movable constructions.

It is unavoidable in this respect that a certain construction effort is exerted to ensure the compressibility of such a pump despite a corresponding reliability and conveying capacity. It must moreover be ensured that large shear forces which can damage sensitive fluids do not arise due to too high a rotational speed of the rotor or due to unfavorable geometrical shapes of impeller blades. In addition, care must be taken that pressure differences within the geometry of such a conveying device, on the one hand, and over the course of time, on the other hand, are kept within tight limits.

BRIEF SUMMARY OF THE INVENTION

Under these conditions and against the background of the prior art, it is the underlying object of the present invention to provide a conveying device which can be manufactured with means which are simple from a construction aspect and which reliably and gently allow the conveying of a fluid.

The object is achieved in accordance with the invention by the features of claim 1.

The conveying device in accordance with the invention, which serves to move a fluid in a conveying direction, for this purpose has a drive body which can be driven by means of a drive system and which can be driven in an oscillating manner transversely to the conveying direction.

The drive body is arranged in a channel or in a space in which the fluid should be conveyed in a preset conveying direction.

Known conveying mechanisms such as centrifugal pumps or the above-named axial flow pumps make use of rotating conveying elements for moving or accelerating a fluid. The likewise known piston pumps respectively have at least one piston which is substantially movable in translation and which conveys the medium in its direction of movement on its movement.

In contrast to this, in accordance with the present invention, the drive body is moved transversely to the conveying direction in the manner of a fin of a fish which is used in nature as a rule to generate a relative movement between the fin and a fluid. In the present invention, the fin-like element, the drive body, is in this respect substantially fixed in the conveying direction so that the relative movement results in a conveying movement of the fluid.

The movement of the drive body transversely to the conveying direction in this respect, for example, means that at least one part of the drive body is moved in translation or along a less curved path substantially perpendicular to the conveying direction and/or associated with a pivot movement about an axis which is substantially perpendicular to the conveying direction. In this respect, the deviation of the direction of extent of the axis to the perpendicular of the conveying direction should amount to a maximum of 45°. In this respect, movement patterns of fin-like bodies in fish and other creatures known from bionics should be reproduced.

The corresponding drive bodies can be adapted in shape and size to the available space. The relative movement of the drive body or of different parts of said drive body with respect to the fluid to be driven can be kept in a range with respect to the speed which prevents the creation of unpermitted shear forces. In this respect, the relative speed is to be coordinated with the viscosity of the medium to be conveyed and accordingly with possibly present compressibilities. The conveying principle described can be used particularly efficiently with substantially non-compressible and slightly liquid media such as blood. Corresponding drive movements can also be transmitted easily to a drive body to be moved in an oscillating manner. A rotatable journalling of a rotor does not necessarily have to be provided.

Since a certain periodicity of pressure fluctuations is to be expected due to the oscillatory movement of the drive body, with an occasional reversal of the flow direction not always being able to be precluded on such pressure fluctuations, the arrangement of a control valve for the flow to be generated in the conveying channel or in the space in which the drive body is located can also advantageously be considered. In this respect, the valve can either be controlled by an intelligent control synchronously with the movement of the drive body or it can be configured as an automatically acting check valve.

The conveying surface or a conveying surface of the drive body is advantageously aligned so that a partial force acts on the fluid in the conveying direction on a movement of the drive body. For this purpose, the direction of movement of the drive body and the direction of extent of the surfaces of the drive body at which a pressure increase arises are to be correspondingly coordinated with one another.

In this connection, at least two conveying surfaces can be provided, for example at a single drive body, which are aligned so that they each effect a conveying of the fluid in at least one of the directions of movement of the drive body. A conveying of the fluid in both drive movement directions or in a plurality of drive movement directions thus becomes possible.

Provision can moreover advantageously be made that at least one drive body tapers in the conveying direction in the cross-section disposed parallel to its movement plane.

The drive body can, for example, be configured in the manner of a fin as a wedge-shaped body whose thickened end is arranged upstream with respect to the flow to be produced and whose tapered end is arranged downstream. The tapered end can converge acutely in the form of a blade edge, with the blade edge being able to extend perpendicular to the drive direction of the drive body. The drive body can also be widened toward its tapered end in the direction of extent of the cutting blade.

The conveying surfaces at both sides of such a wedge-shaped fin body can be either planar or convex or concave, viewed in the direction perpendicular to the drive direction of the drive body.

The drive body can be stiff in one type of embodiment of the invention. In this case, the drive body can be pivotable about an axis which lies in the region of its thickened end. In addition, a superimposed movement in translation of the thickened end can be provided, for example in a straight manner or along a gate path. The movement portion in translation takes place in the same plane as the pivot movement in this respect.

Alternatively to this, provision can also be made that the drive body is so elastic that it can also be bent in operation in its end region by the fluid counterpressure by at least 5°, in particular also by at least 20°, with respect to the undistorted state.

The drive can in this case be configured in the same manner as with a stiff drive body, but the alignment of the conveying surfaces relative to the fluid to be conveyed in the respective phase of the drive movement can already be optimized and thus the efficiency of the drive increased by the elasticity and deformability of the drive body per se.

Such a drive body, whether stiff or elastic, can either be configured as symmetrically wedge-shaped, with planar, concave or convex conveying surfaces in the cross-section viewed perpendicular to the plane of the drive movement or a shape asymmetrical in the named cross-section can also be provided, for example with elements of an airfoil wing, to utilize additional flow effects. Such an airfoil section, for example, provides a convex shape on one side of the drive body and a convex or straight shape of the conveying surface on the opposite side.

On the use of such an asymmetrical design of a drive body, a further drive body can additionally be provided which is shaped and arranged in mirror form with respect to the first drive body and which is movably in synchronization with it in the same or opposite sense.

Provision can moreover be made to increase the efficiency of the drive that the drive body, in particular in the region of a conveying surface, has optimized surface structures.

In an advantageous embodiment of the invention, provision can moreover be made that the drive body has at least one hollow space. The provision of a hollow space reduces the mass of the drive body and thus the energy to be expended for its acceleration. In addition, the drive body can be configured as at least partially inflatable so that its outer dimensions in the non-inflated state can be smaller than in the inflated state. Such a drive body can then be brought more easily to its deployment site in the non-inflated state and inflated to the operating dimensions there. This is in particular advantageous when the conveying device should be manufactured in very small dimensions and moved within blood vessels.

The drive body can moreover advantageously comprise a foam, in particular polyurethane. The drive body can thus be manufactured as elastically deformable and as very light.

Provision can be made in the conveying device in accordance with the invention by providing a corresponding drive system that the drive body can be driven by means of a hydraulic or pneumatic device, in particular by means of a balloon body, but also by means of an electric and/or magnetic device.

Although one or more drive bodies in accordance with the invention can be moved simply by means of levers or similar mechanical devices, the drive movement can particularly easily be conducted to the conveying device by a hydraulic or pneumatic drive device. Corresponding pneumatic or hydraulic lines can be laid, for example, in the form of a hollow catheter or also within a hollow catheter, at the distal end of which the conveying device is provided, and can either act directly on a piston, bellows or balloon-like drive body in the region of the conveying device or can be converted into a lever movement there.

Possible drive movements of the drive body or bodies in this respect provide that at least one drive body is pivotable in an oscillating manner about an axis extending transversely to the conveying direction; and/or that one or more drive bodies are pivotable in an oscillating manner about an axis extending in the conveying direction, in particular outside the conveying bodies.

It is special about such an oscillatory movement that the pivot movement has a relatively small stroke so that a full rotation of the drive body does not take place in any case.

A rotation about larger angles can, however, also be provided on the rotation about an axis extending in the conveying direction.

To reduce unwanted pressure compensation procedures at the drive bodies, blocking bodies can be arranged on them between their conveying surfaces. Said blocking bodies should be flexible and can in this respect be configured as pliable or stiff, but bendable. The blocking bodies can also connect two respective blocking bodies to one another or one blocking body to a housing wall.

The described fin-like drive principle for fluids is novel in connection with the conveying of liquids and thus allows the realization of conveying characteristics which cannot be achieved with the already known conveying devices.

BRIEF DESCRIPTION OF THE DRAWINGS

The invention will be shown and subsequently described in the following with reference to an embodiment in a drawing.

There are shown in

DETAILED DESCRIPTION OF THE INVENTION

Figure 1:
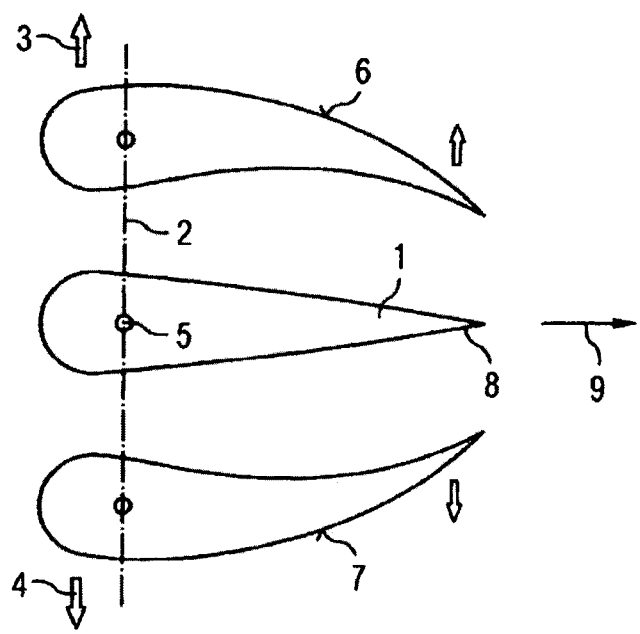
FIG. 1 a drive body in three positions in cross-section.

FIG. 1 shows in the middle part a drive body 1 in section which substantially has a wedge shape which is modeled on the shape of a fin occurring in biology. The drive body 1 extends perpendicular to the plane of the drawing with an unchanging section, but can also widen perpendicular to the plane of the drawing toward its tapered end.

The drive body 1 can be moved in an oscillating manner along the dotted line 2 in the directions indicated by the arrows 3, 4. The region about the point of attack of the driving force is in this respect shown as a circle and is marked by 5. The driving force engages at this point such that the drive body is moved substantially in translation along the line 2 and is thus not pivotable in a first variant to avoid an active fluid counterpressure.

A fluid counterpressure then results in operation, for example on the movement of the drive body within a liquid, on the side of the respectively acting conveying surface 6, 7, said fluid counterpressure resulting in a deformation of the end 8 of the drive body 1 remote from the drive, i.e. the tapered end, when this drive body is configured as elastic as in the example shown. A particularly efficient advance of the driven fluid in the conveying direction 9 results by this effect.

Alternatively, the drive of the drive body 1 can also be configured so that it is not driven strictly in translation in the sense of the directions 3, 4, but rather in a superimposed movement in translation and in a pivot movement. In this respect, for example simultaneously with the movement in the direction of the arrow 3, a pivoting of the drive body takes place about the point of attack 5 clockwise about a specific angle, for example 10°, so that the drive body inclines at the end of the movement in a similar manner as under the effect of a fluid counterpressure. Optionally, the direction of rotation of the pivot movement can be reversed at the end of the movement in translation to beat with the fin. This driving principle can be combined both with stiff drive bodies and with flexible drive bodies.

A specific lever drive or a gate drive of the drive body can be provided for this purpose or it is conceivable to transmit the driving forces by means of a hydraulic or pneumatic apparatus.

Figure 2:
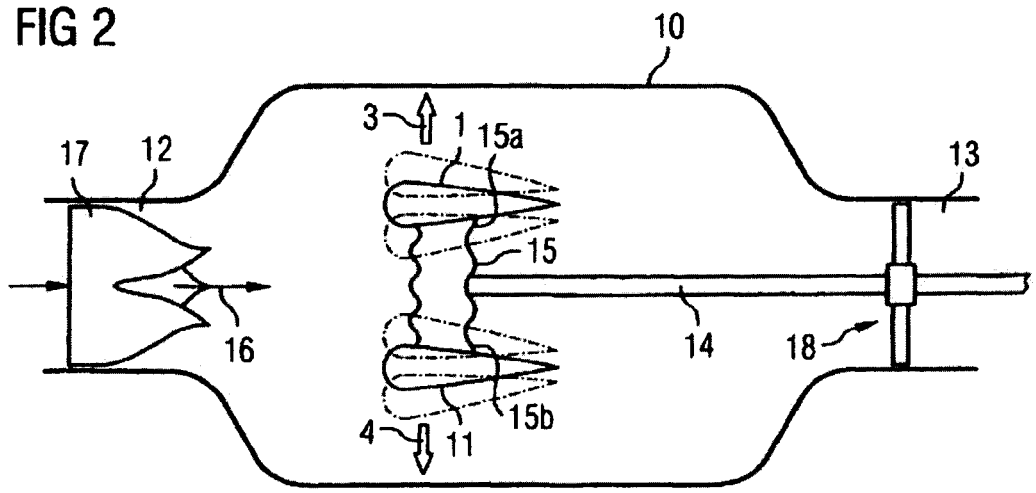
FIG. 2 a conveying system for fluids having two drive bodies in a longitudinal section.
Figure 3:
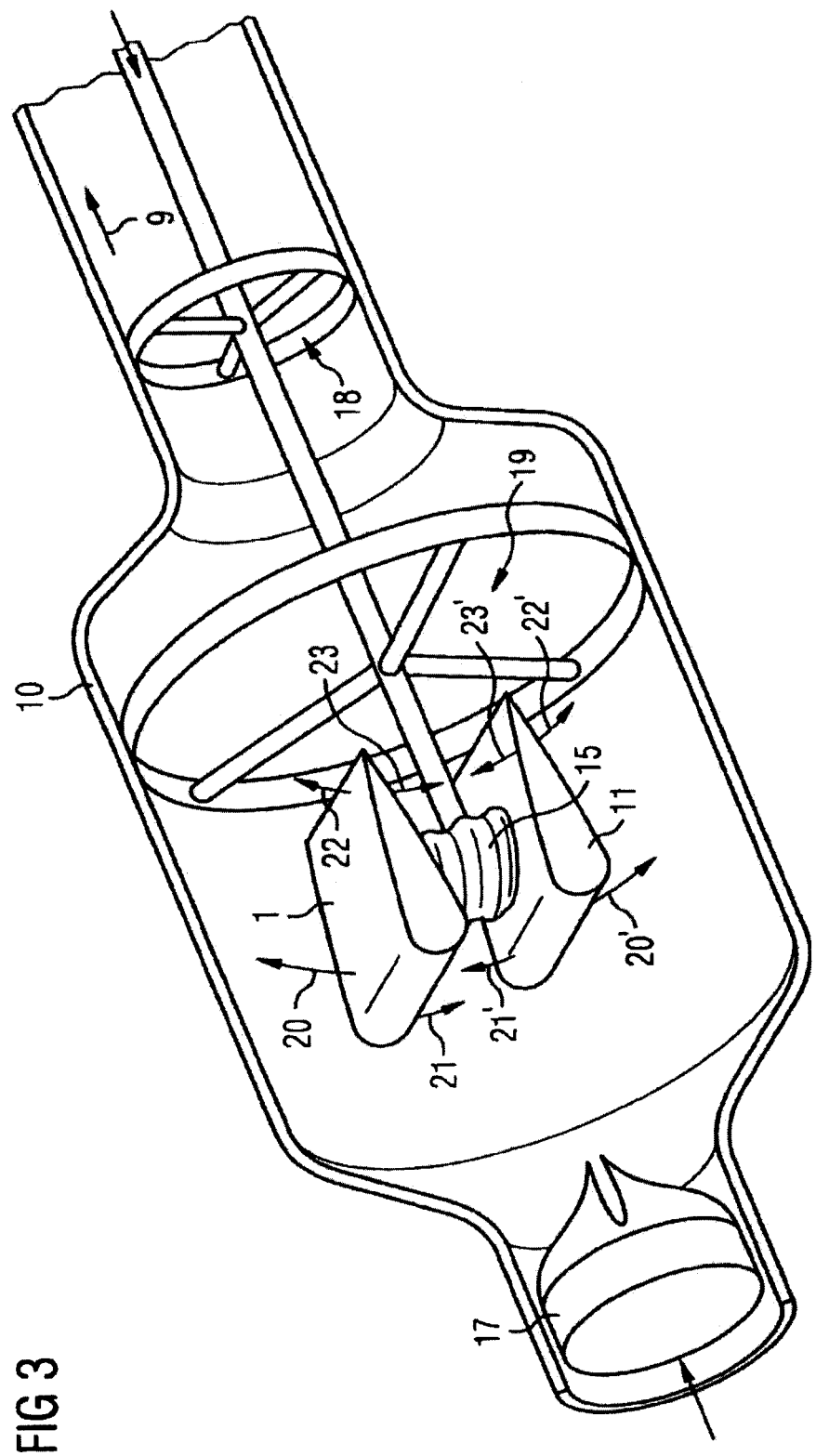
Figure 7:
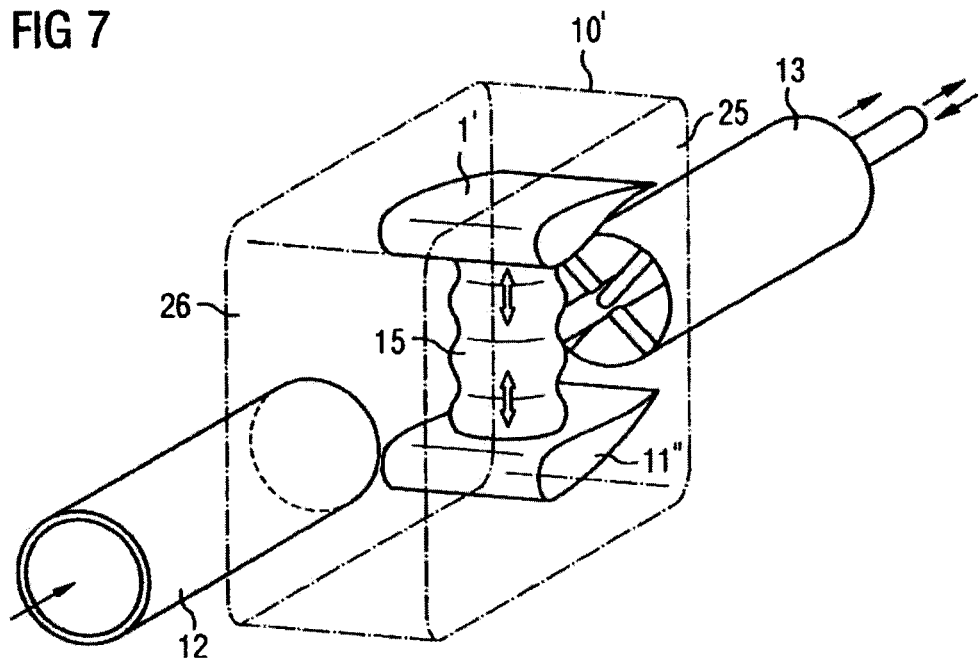
Figure 8:
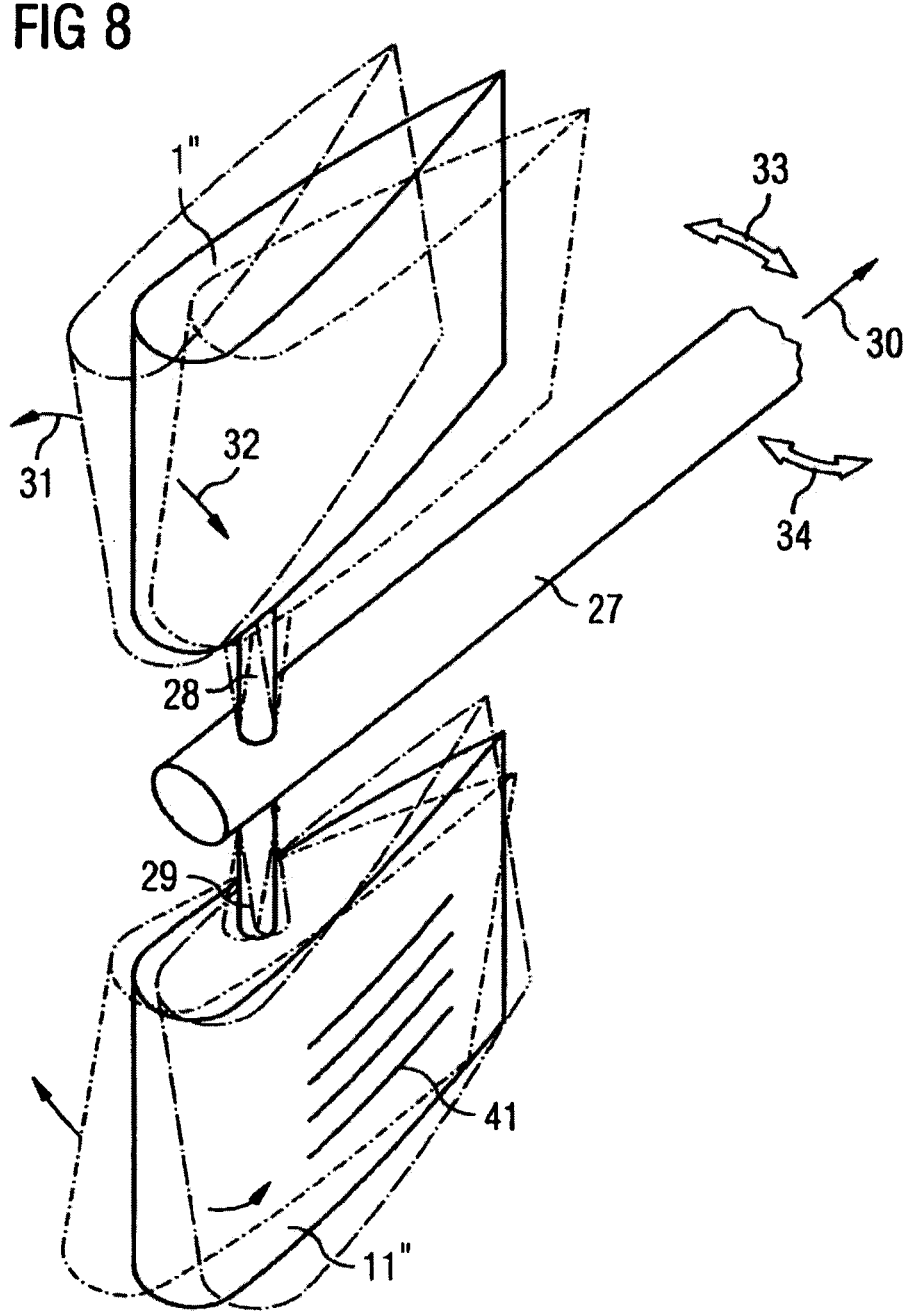
Figure 9:
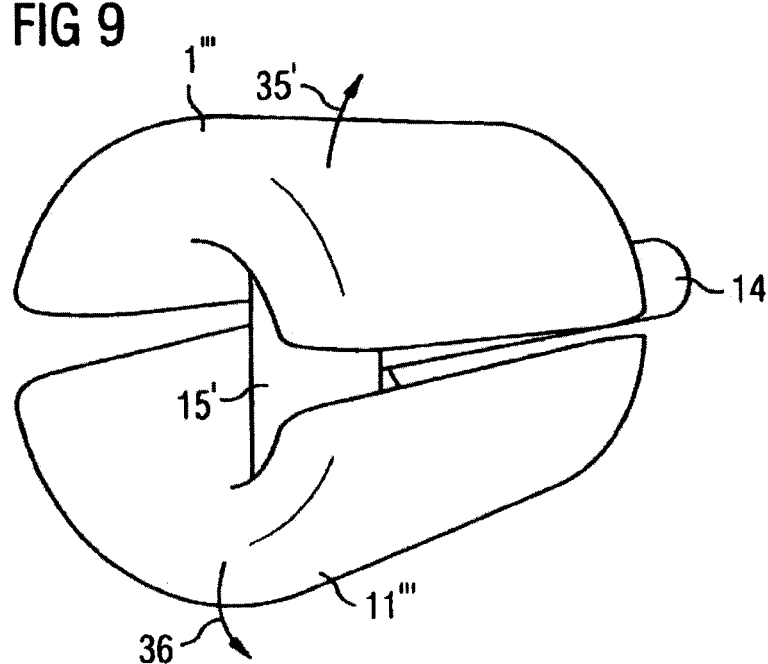
Figure 10:
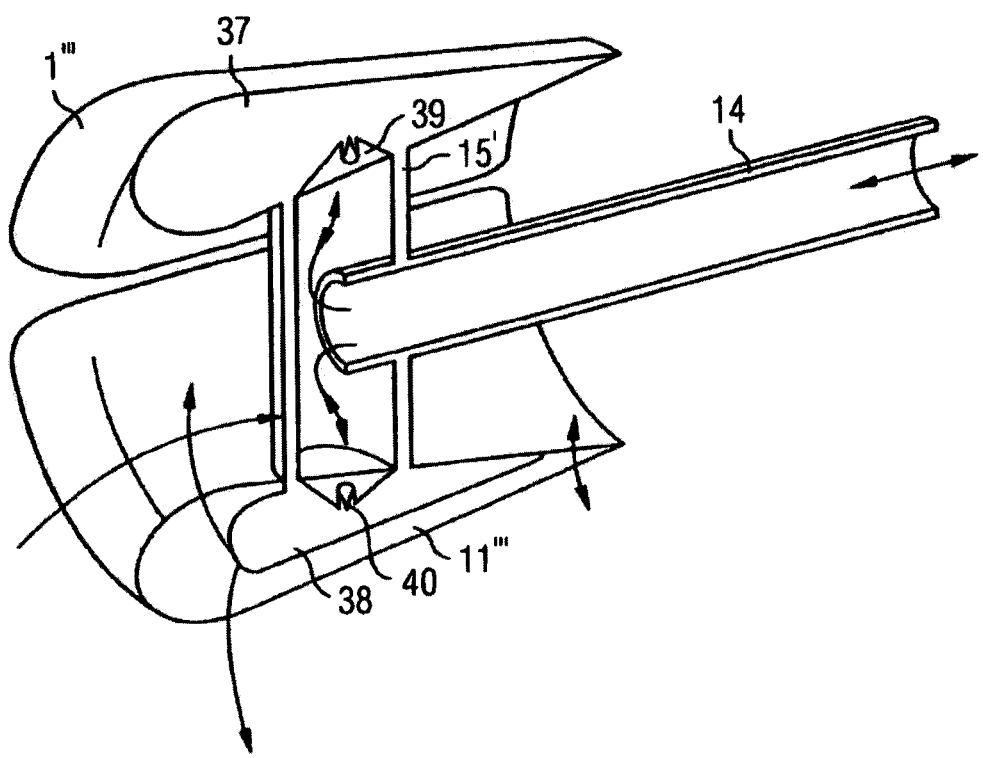
Figure 12:
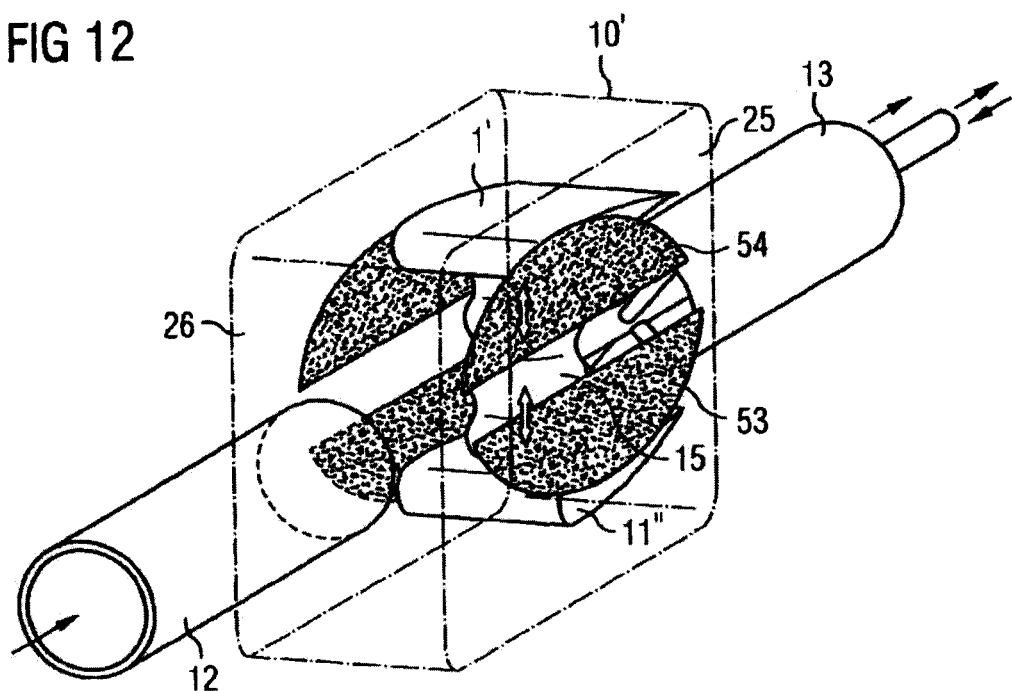
Figure 13:
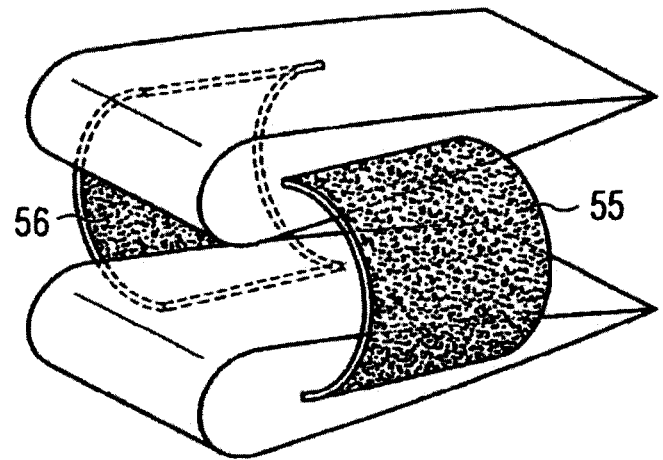
Figure 14:
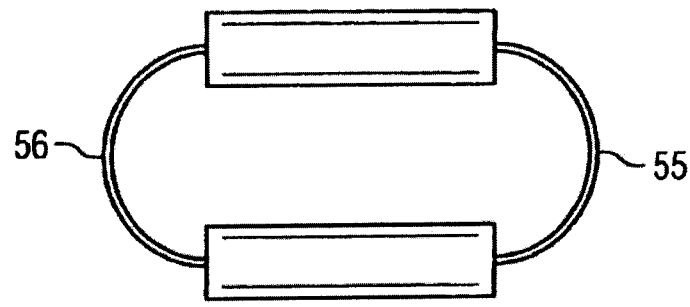
Figure 15:
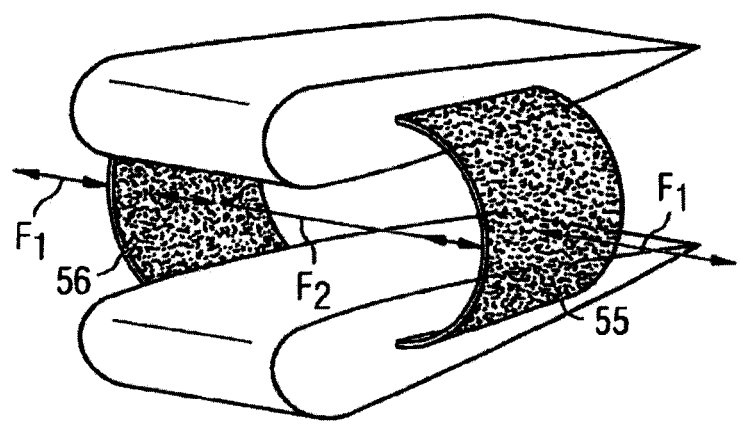
Figure 16:
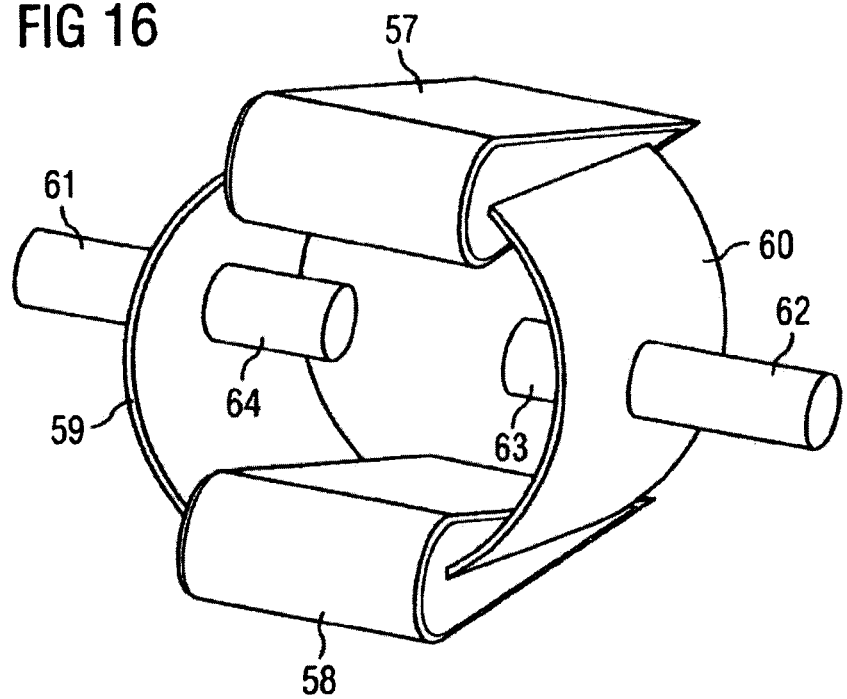
Figure 17:
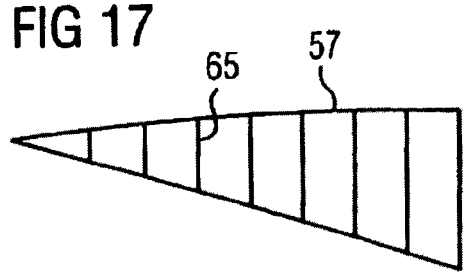
Figure 18:
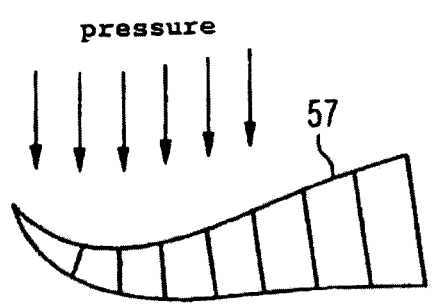

FIG. 2 shows in a side view a housing 10 in which a conveying device in accordance with the invention having two drive bodies 1, 11 is arranged. The housing 10 is set up rotationally symmetrically or elliptically in cross-section about the drive bodies 1, 11 and has an inflow channel 12 as well as an outflow channel 13. A fluid line 14 which is part of the drive system and which is connected to a drive bellows 15 projects through the outflow channel 13. The drive bellows 15 can be connected via a pressure control device, not shown, via the fluid line 14 to an overpressure or to an underpressure so that said drive bellows can be inflated or deflated by the inflow of a fluid or the removal of the fluid.

One respective drive body 1, 11 is fastened to the two ends 15a, 15b of the drive bellows 15 and runs through a drive movement in the direction of the arrows 3, 4 by the volume changes of the drive bellows. The drive movement in translation of the drive bellows 15 can be translated into a more complex movement path of the drive bodies 1, 11, which can correspond to a superimposition of the movement in translation with a pivot movement, by a corresponding elastic configuration of the drive bellows 15 or by additional levers which connect the bellows to the drive bodies 1, 11 or the drive bodies to a fixed point of the housing 10.

Provision can, however, also be made that the movement of the drive bodies 1, 11 substantially takes place in translation and said drive bodies are configured as elastic to carry out the elastically fin-like overall movement shown with reference to FIG. 1.

If the pressure in the drive bellows 15 is changed periodically via the control of the fluid pressure in the fluid line 14, for example several times per second, this is translated into an oscillatory movement of the drive bodies 1, 11. This results in an acceleration of the fluid located in the housing 10 in the direction of the arrow 16 which designates the conveying direction of the fluid. Since pressure fluctuations occur due to the periodicity of the movement, it may be meaningful to provide a check valve 17 in the inflow channel 12 which blocks the inflow channel 12 for the case that an overpressure arises within the housing 10 in front of the valve and closes it again as soon as an underpressure is generated there.

The fluid line 14 can be configured as a flexible hose line provided that the drive bellows 15 is held otherwise in the housing 10. The drive line 14 can, however, also be configured as a rigid line in the form of a pipe in order simultaneously to conduct the fluid and to fix the drive bellows and the drive bodies 1, 11. The fluid line 14 can in every case be held and fixed in a holding star 18 or at a holding arm within the outflow channel 13.

In the Figure, three positions are shown for each drive body 1, 11, with a middle neutral position being shown by solid lines and the extreme positions on the movement path of each individual drive body 1, 11 being shown by broken lines.

Figure 3:
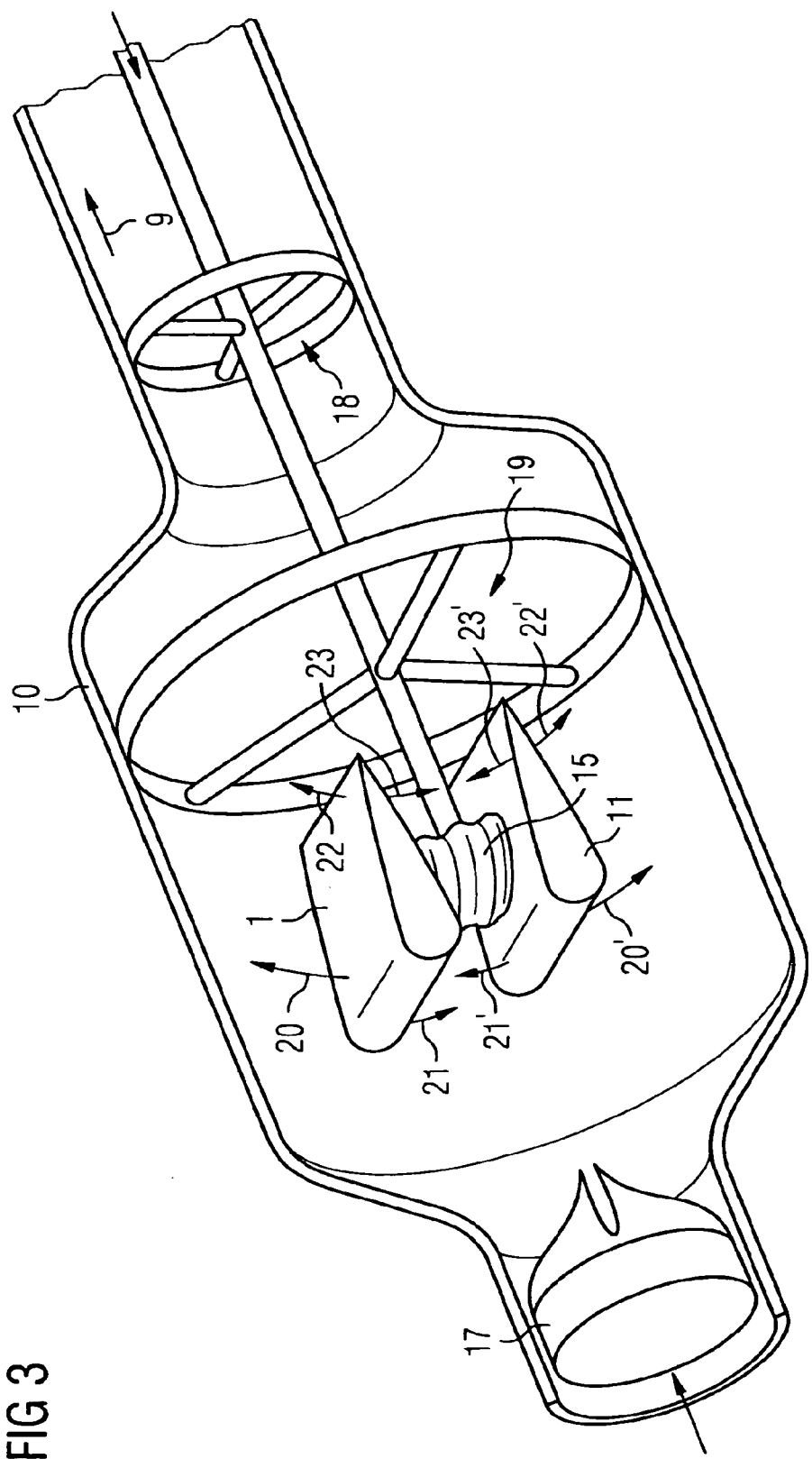
FIG. 3 a conveying system having two drive bodies in a three-dimensional view.

FIG. 3 shows a similar arrangement to FIG. 2, but in a three-dimensional view, with a second holding star 19 being provided in addition to the first holding star 18 in direct vicinity of the drive bellows 15 and of the drive bodies 1, 11.

Arrows 20, 21 and 20', 21' are drawn in which indicate the directions of movement of the respective thickened ends of the drive bodies 1, 11 as are arrows 22, 23 and 22', 23' which indicate the movement of the tapered ends of the drive bodies 1, 11. The different lengths of the arrows shown should indicate that the thickened ends of the drive bodies 1, 11 facing the one-way valve 17 carry out a pivot movement whose amplitude is substantially larger than the movement of the tapered ends of the drive bodies. This is made possible, as will be shown in more detail with reference to FIGS. 4, 5 and 6, by a special construction of the drive bellows 15.

Figure 4:
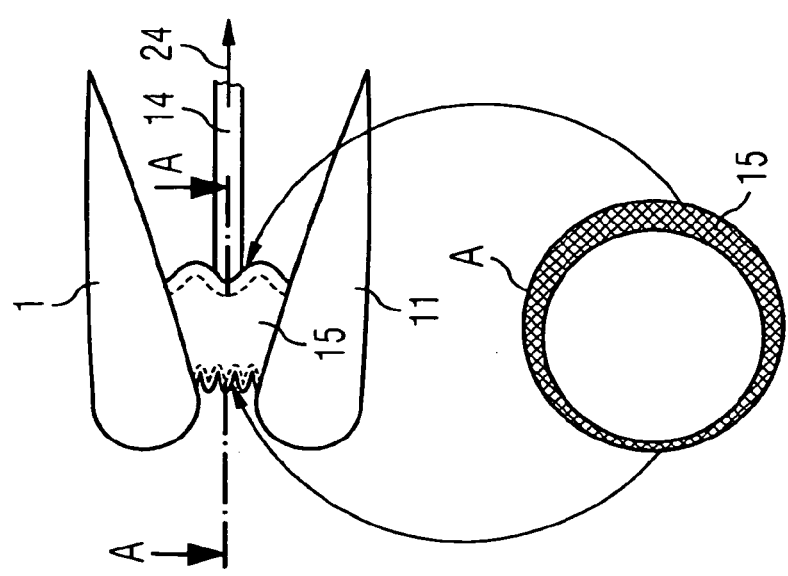
FIG. 4 two drive bodies in a first position with a drive system.

FIG. 4 shows in a side view in the upper part the two drive bodies 1, 11 as well as the drive bellows 15 in the deflated, i.e. compressed, form. The arrow 24 indicates that an underpressure is present in the fluid line 14 in this state to compress the drive bellows 15.

The drive bellows 15 itself has an asymmetrical structure, as can be seen more clearly from the lower part of FIG. 4. A cross-section through the drive bellows 15 along the dashed line A is shown there which makes clear that the drive bellows has a smaller wall thickness in its region facing the one-way valve 17 than in the outflow channel 13.

It is thereby achieved that the movement amplitude is larger in the front region facing the inflow channel 12 than in the rear region of the drive bellows facing the outflow channel 13. A pivot movement of the drive bodies 1, 11 therefore results on a pressure change in the drive bellows 15.

Figure 5:
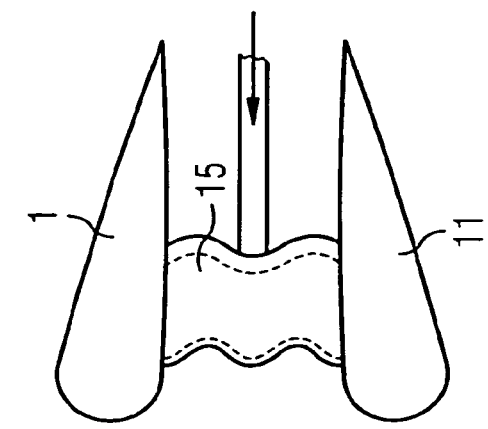
FIG. 5 the drive bodies from FIG. 4 in a second position.

In FIG. 5, the arrangement of FIG. 4 with the drive bodies 1, 11 and a drive bellows 15 inflated further with respect to FIG. 4 is shown. The drive bodies are approximately in the straight position shown in FIG. 2.

Figure 6:
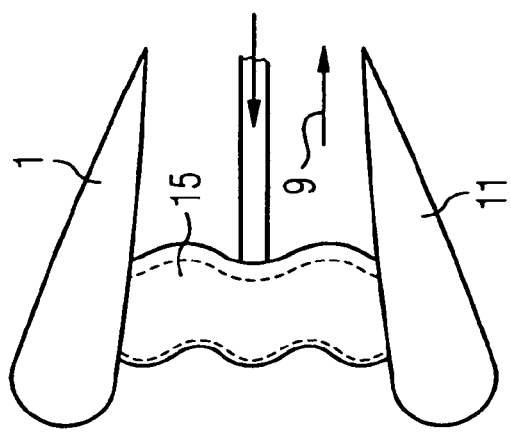
FIG. 6 the drive bodies from FIGS. 4 and 5 in a third position.

FIG. 6 finally shows the state of the drive bodies 1, 11 in the fully inflated state of the drive bellows 15, with it also becoming clear that the thickened ends of the drive bodies 1, 11 have passed through a larger movement amplitude than the tapered ends so that a pivot movement of the drive bodies has taken place in addition to a movement in translation.

Figure 7:
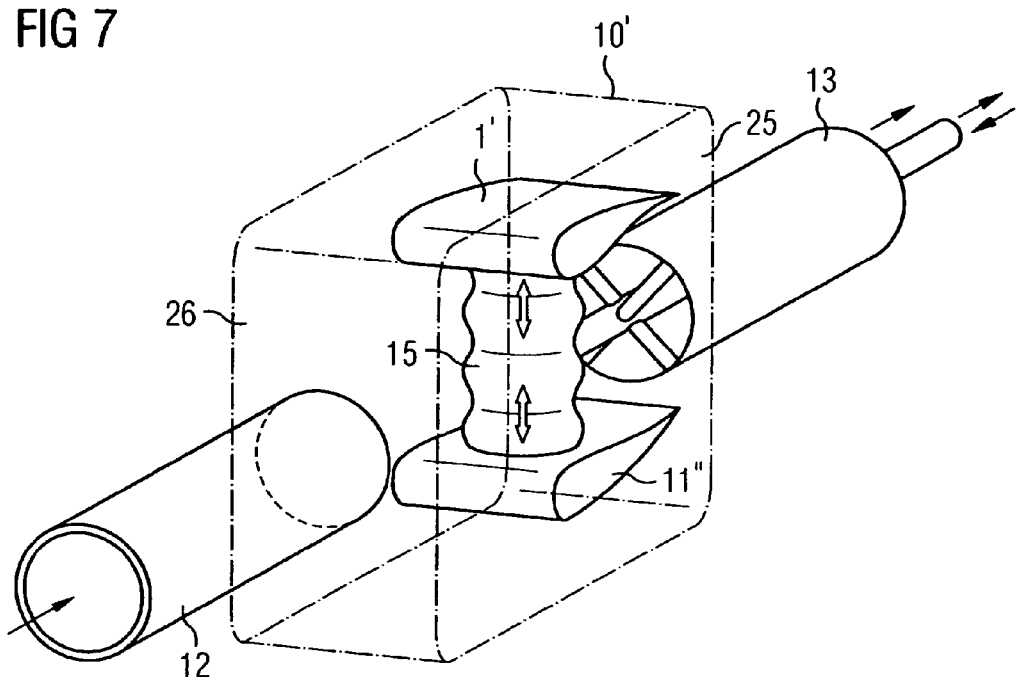
FIG. 7 a drive system in a three-dimensional representation having a conveying space quadrangular in cross-section.

FIG. 7 shows in a three-dimensional view from a different perspective two drive bodies 1', 11' which are configured as asymmetrical in the manner of an aerodynamic airfoil section, but which may additionally also be configured as flexible and which can be driven by means of a drive bellows 15. The inflow channel 12 is shown in the foreground of the figure, the outflow channel 13 in the background. In contrast to the cylindrical housing 10 of the arrangement shown in FIG. 3, the housing 10' shown in FIG. 7 has a parallelepiped structure with a rectangular cross-section to implement the non-cylindrically symmetrical structure of the drive arrangement and of the drive bodies as efficiently as possible. Unlike the specific representation of FIG. 7, the transition from the housing 10' to the inflow and outflow channels 12, 13 can take place with conical or oblique transitions. Provision can advantageously be made that the drive bodies 1', 11' extend perpendicular to the plane of the drive movement up to as close as possible to the side walls 25, 26 of the housing 10'. Turbulence at the side surfaces of the drive bodies 1', 11' is thereby reduced.

The drive bodies 1', 11' can, just like the drive bodies 1, 11 shown further above, comprise a foam, in particular polyurethane, and can be inflatable. For this purpose, the bodies can have large and/or a plurality of small hollow spaces which can, for example, be inflated by the drive fluid via the fluid line 14 and which have check valves to be stabilized in the inflated state.

A good compressibility in the non-inflated state is hereby made possible so that the drive bodies can be radially compressed for transport to a deployment site together with the housing 10, 10' and can be expanded on site before they are put into operation.

Figure 8:
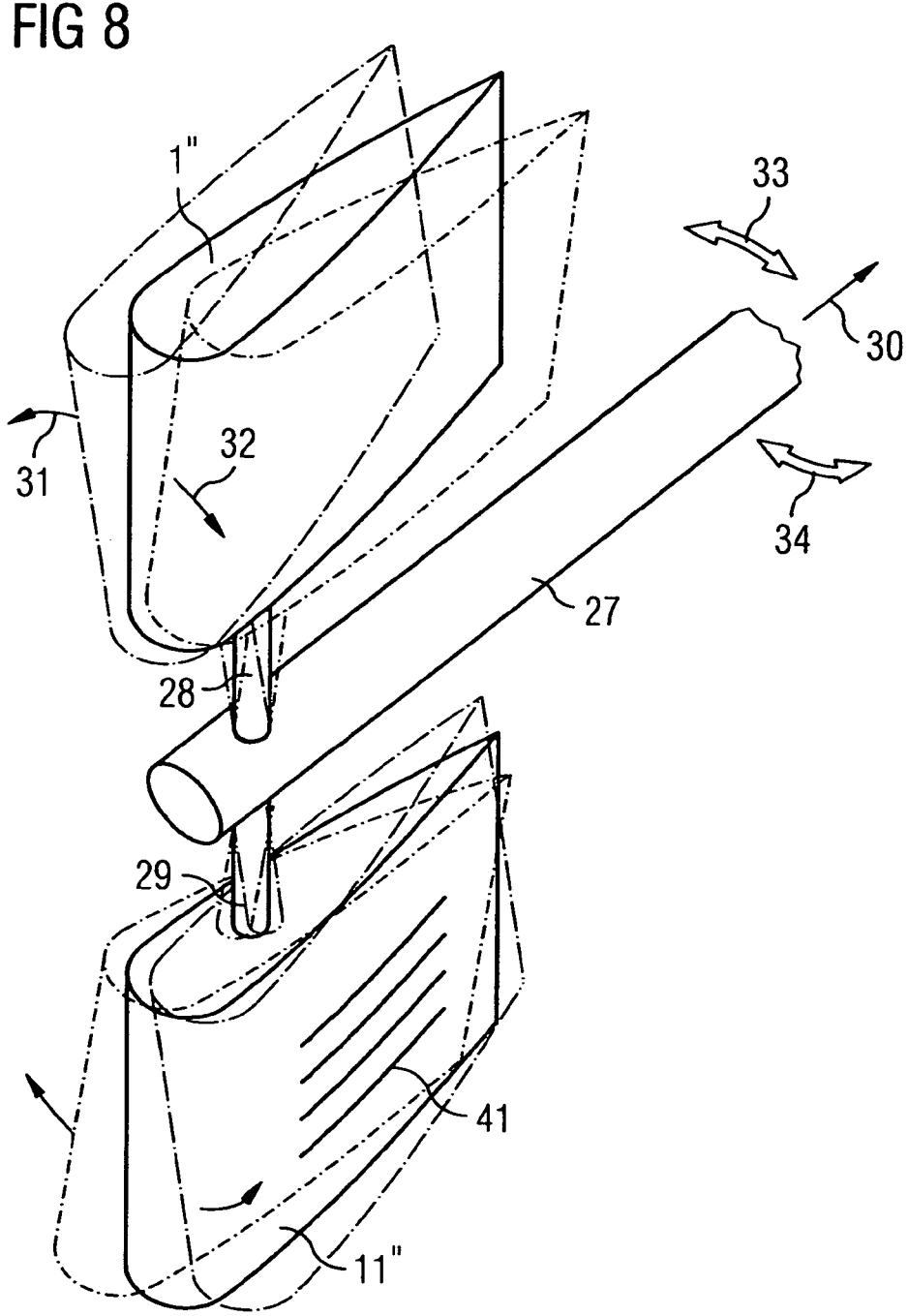
FIG. 8 two drive bodies which are rotated in an oscillating manner about an axis extending in the conveying direction.

FIG. 8 shows an arrangement in comparison with the Figures described further above having two drive bodies 1", 11" with another drive principle in which the drive bodies are connected via connection webs 28, 29 to a drive shaft 27 which extends in the conveying direction 30.

The drive shaft 27 can be rotated in an oscillating manner about the conveying direction 30, and indeed in each case, for example, at least by an amount of 5°, 10° or at least by 20° or 30°, in each direction, as indicated by the arrows 33, 34.

The longitudinal axes of the drive bodies 1" and 11" are aligned parallel to the shaft and undergo a movement quasi in translation in the peripheral direction of the shaft in the directions which are indicated by the arrows 31, 32 within the framework of this rotary movement, provided that the length of the connection webs 28, 29 is sufficient. In this manner, a corresponding approximately linear movement in translation of the drive bodies can be realized in a very simple manner by means of the drive shaft 27. In FIG. 8, a plurality of parallel microgrooves 41 are also shown by way of example at the lower drive body 11".

Figure 9:
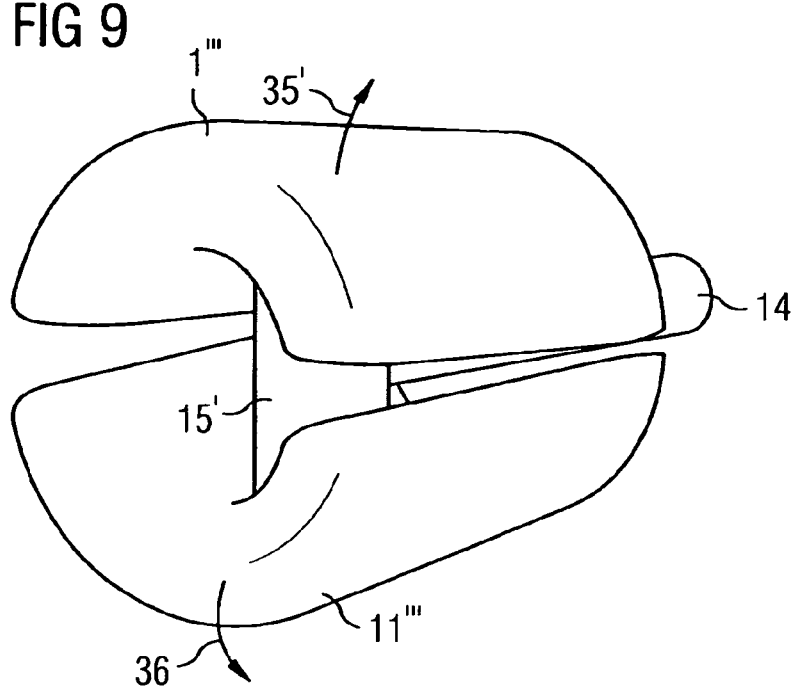
FIG. 9 a drive system in a three-dimensional view having two partly cylindrical drive bodies.

In FIG. 9, an arrangement is shown in a three-dimensional view which is as largely cylindrically symmetrical as possible of two drive bodies 1''' and 11''' which are connected by a drive bellows 15' and which can be moved substantially in the direction of the arrows 35, 36 in the radial direction with respect to the cylinder axis. The drive bellows 15' is connected to a pressure generation system by means of a fluid line 14. It is also conceivable to divide the cylindrically symmetrical arrangement into a higher number of cylinder segments, for example 4 or 8 or more and to move them radially in each case, with a movement pattern resulting which is similar to the manner of propagation of jellyfish.

Figure 10:
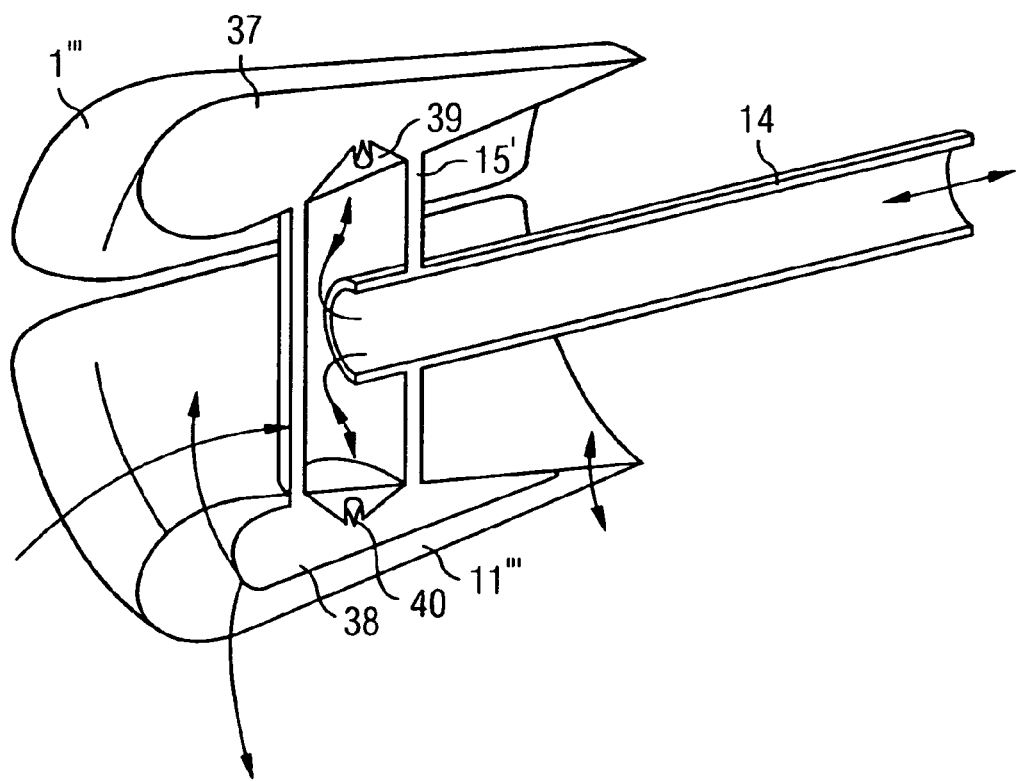
FIG. 10 a section through the drive system of FIG. 9.

A section through the arrangement of FIG. 9 is shown in FIG. 10 which makes the function clear. The drive body 1''' is shown by way of example with a hollow space 37, the drive body 11''' with a hollow space 38, with the hollow spaces only being indicated schematically.

Fluid is exchanged via the fluid line 14 with the interior of the drive bellows 15 and is pumped from there into the hollow spaces 37, 38, with the hollow spaces 37, 38 of the drive bodies 1''' and 11''' being connected to the hollow space of the drive bellows 15' by means of one-way valves 39, 40 so that the drive bodies are only inflated once and then thereafter maintain the increased fluid pressure to be stabilized in shape. Only the interior of the drive bellows 15' is inflated and deflated thereafter. The drive bodies 1''', 11''' thereby alternately move apart in the direction of the arrows 35, 36 and move together in the opposite direction, whereby a corresponding drive movement is realized.

The efficiency of the conveying device with respect to the non-cylindrically symmetrical arrangements which are shown in the aforesaid Figures is increased by the cylindrically symmetrical or approximately cylindrically symmetrical arrangement of the drive bodies.

Figure 11:
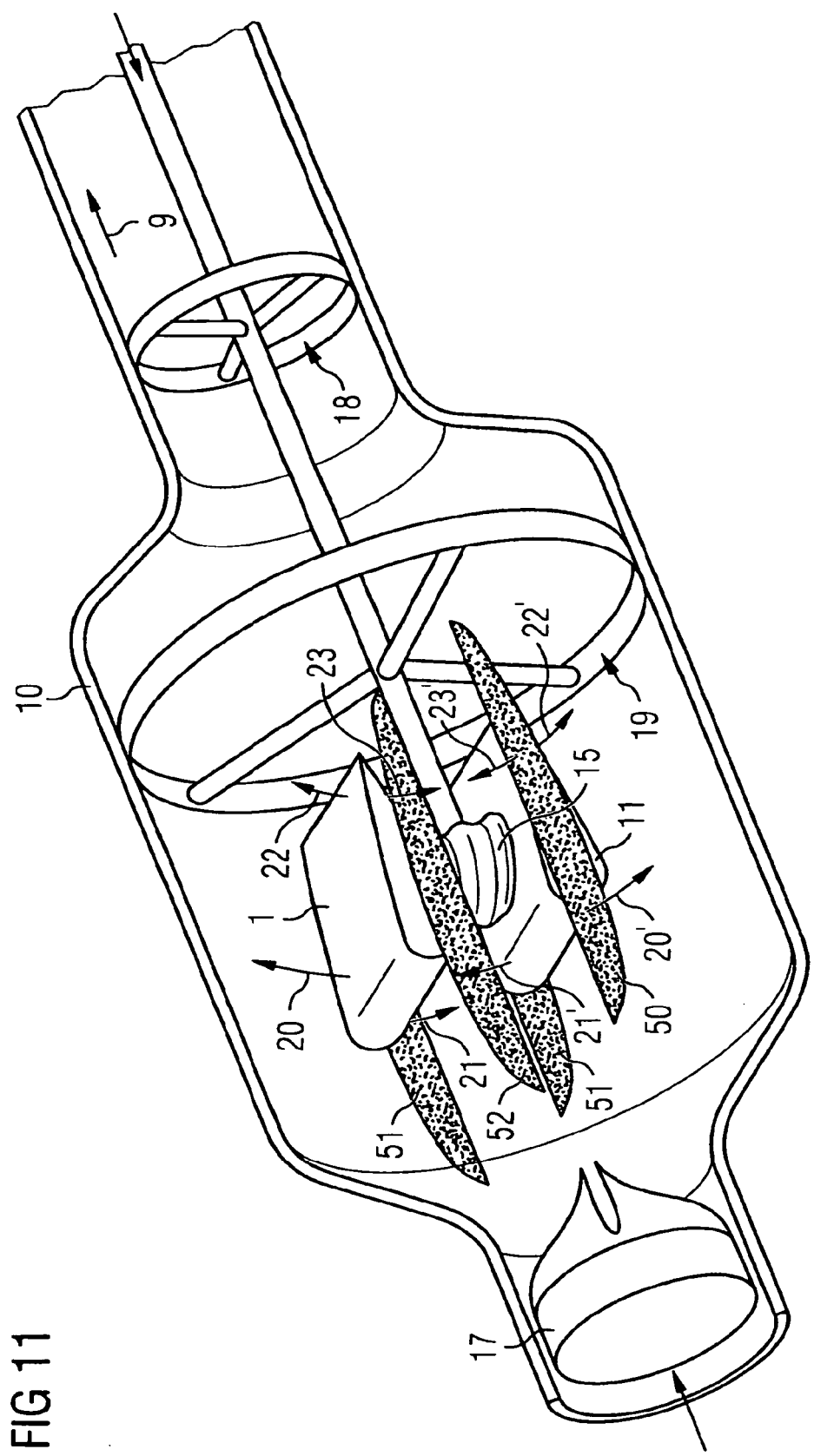
FIG. 11 an embodiment as in FIG. 3 with additional blocking bodies.

FIG. 11 shows a cylindrical arrangement of a housing 10 having two drive bodies 11 which are each laterally provided with blocking bodies 50, 51, 52, 52 which are flexible and may also be connected to the wall of the housing 10 and which prevent or reduce a pressure equalization between the lower side and upper side or the high pressure side and low pressure side of each drive body during the drive movement.

Figure 12:
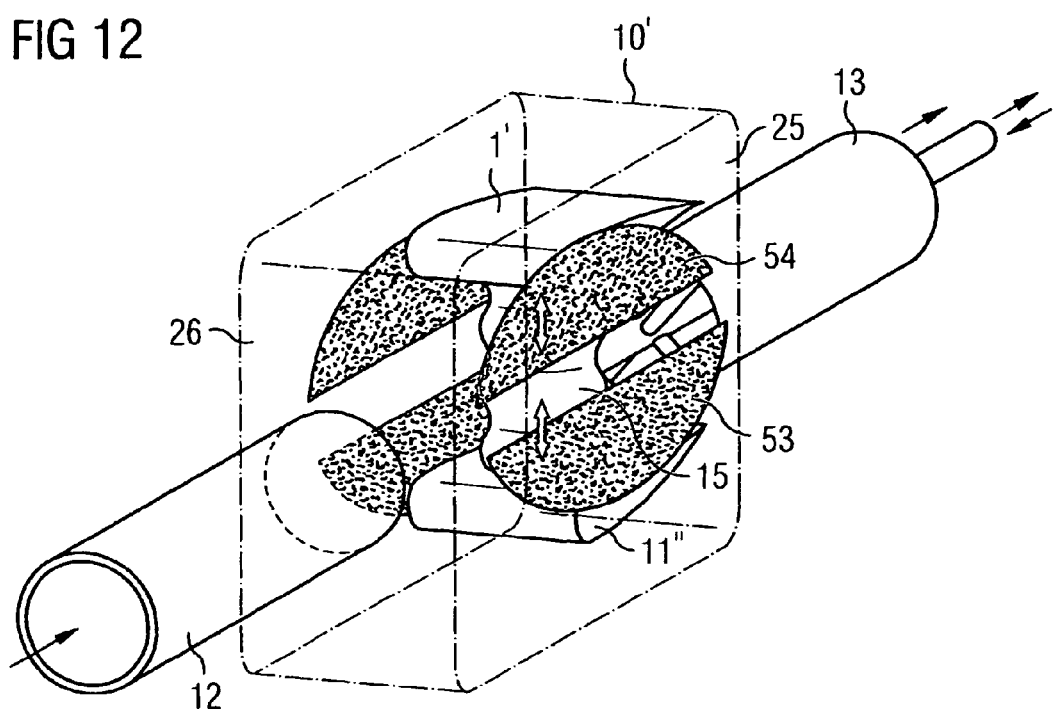
FIG. 12 an embodiment similar to that of FIG. 7 with blocking bodies.

FIG. 12 shows corresponding blocking bodies 53, 54 for a housing 10' with flattened side walls.

Figure 13:
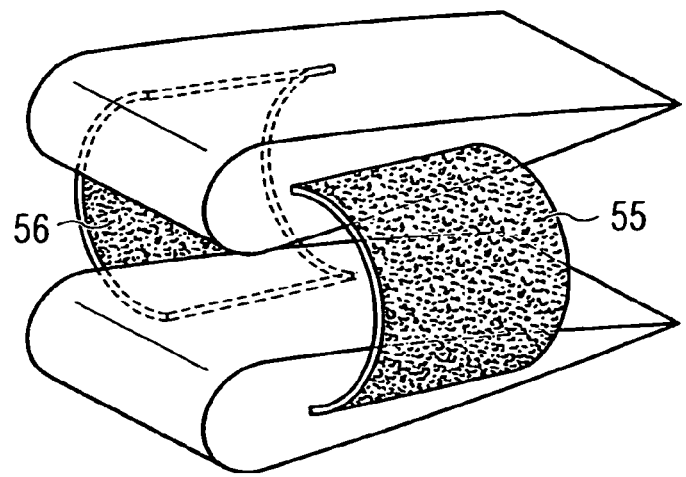
FIG. 13 a representation of two drive bodies which are connected by means of blocking bodies.

FIG. 13 shows two blocking bodies in the form of wide, flexible bands 55, 56 which connect two drive bodies to one another at both sides. This constellation is shown in a front view in FIG. 14.

Figure 15:
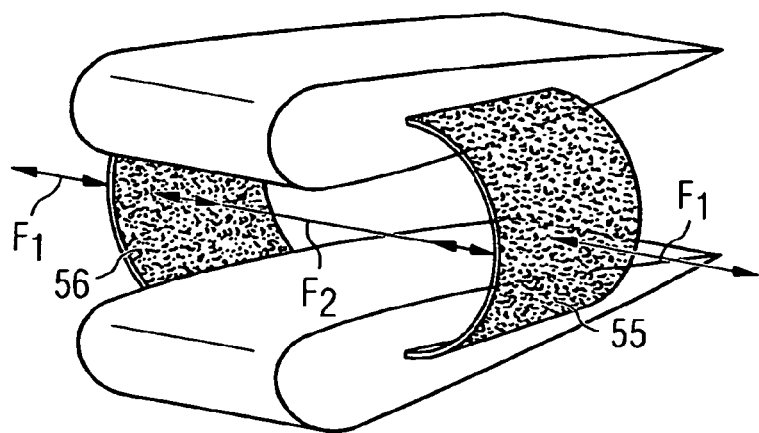
FIG. 15 a view of the embodiment of FIG. 13, with the effect of a driving force on the blocking bodies being indicated.

FIG. 15 shows two blocking bodies 55, 56, as in FIG. 13, which connect two fin-like drive bodies to one another and act as an equalization block. The blocking bodies are configured as strips and can be configured as flexible or stiff and elastically pliable. In the latter case, a drive movement can be directly applied to the drive bodies by direct application of a mechanically, magnetically, pneumatically hydraulically or electrically generated driving force onto the blocking bodies from the outside, indicated by the arrows $F_1$ and $F_1'$ or from the inside from the intermediate space of the drive bodies, indicated by the double arrow $F_2$.

Instead of the blocking bodies, similarly positioned coupling bodies in the form of a scaffold or frame can be provided to couple the drive movement into the sections.

Figure 16:
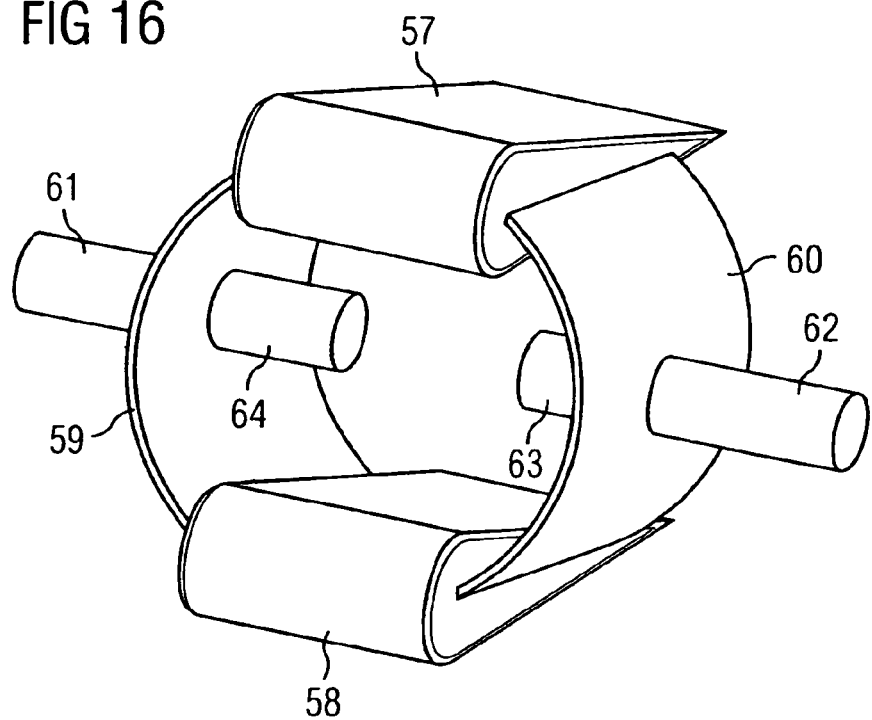
FIG. 16 an arrangement in which the blocking bodies have a stiff, but bendable ring-strip shape.

The principle of the drive via the blocking bodies is additionally illustrated by way of example by FIG. 16. Two drive bodies 57, 58 are connected to one another there by two ring segments 59, 60 of a ring strip in the form of a circular ring. The cylinders 61, 62 symbolically indicate outwardly engaging driving forces which can apply a traction force or a compression force to the ring segments from the outside. Corresponding inwardly engaging forces are symbolically designated by 63, 64. A deformation of the ring segments effects a drive movement of the drive bodies 57, 58. They can be controlled in a suitable manner by a profiling of the ring segments 59, 60 or by cut-outs in the ring segments.

Figure 17:
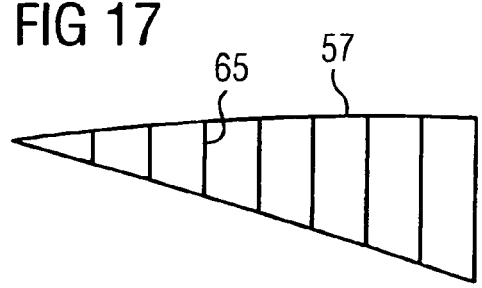
FIG. 17 a drive body having fin-rays in the neutral state.
Figure 18:
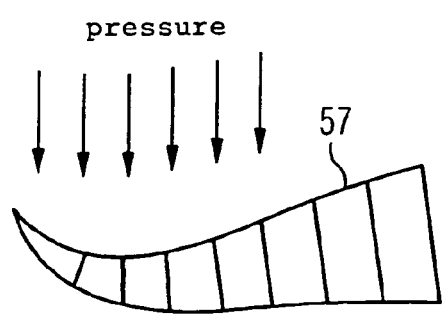
FIG. 18 a drive body as in FIG. 17 in the loaded state.

In FIGS. 17 and 18, a drive body is shown in a schematic plan view having so-called fin-rays 65 which have an influence on the flow of the fluid as web-like, groove-like or fin-like structures on the surface. They can be shaped and configured such that they effect a concave deformation and thus an increase in pressure on the pressure side on a movement of the drive body.

The conveying device for fluids in accordance with the invention allows an efficient configuration thanks to the use of an oscillatory movement transversely to the conveying direction of drive bodies, with the disadvantages of only rotating drive devices being avoided.

The invention claimed is:

1. A conveying device for the conveying of blood in a conveying direction having at least one drive body which can be driven by a drive system and which has a conveying surface, the drive body having a thickened upstream end and a tapered downstream, elastically deformable end, wherein the drive body can be driven in an oscillating, fin-like manner transversely to the conveying direction and is flowed around on a plurality of sides by blood to be conveyed, and wherein the drive body can be compressed together with a housing surrounding it.

2. The conveying device in accordance with claim 1, wherein the drive body/bodies can be driven by a rotatable shaft.

3. The conveying device in accordance with claim 1, wherein the at least one drive body is pivotable in an oscillating manner about an axis extending transversely to the conveying direction.

4. The conveying device in accordance with claim 1, wherein the conveying surface of the at least one drive body is aligned such that a partial force acts on the blood in the conveying direction on movement of the at least one drive body.

5. The conveying device in accordance with claim 4, wherein two conveying surfaces are aligned such that they effect a conveying of the blood in a respective movement direction of the at least one drive body.

6. The conveying device in accordance with claim 1, wherein the at least one drive body tapers in the conveying direction in the cross-section disposed parallel to its movement plane.

7. The conveying device in accordance with claim 1, wherein the at least one drive body is configured as stiff.

8. The conveying device in accordance with claim 1, wherein the at least one drive body is configured as elastic such that it is bendable in its end region by the fluid counter-pressure in operation by at least 5° with respect to the non-deformed state.

9. The conveying device in accordance with claim 8, wherein the at least one drive body has microgrooves extending in the conveying direction.

10. The conveying device in accordance with claim 1, wherein the at least one drive body has at least one hollow space.

11. The conveying device in accordance with claim 1, wherein the at least one drive body comprises a foam.

12. The conveying device in accordance with claim 11, wherein the at least one drive body is at least partly inflatable.

13. The conveying device in accordance with claim 1, wherein the drive body/bodies is/are deformed in operation against the fluid pressure on the respective pressure side/sides.

14. The conveying device in accordance with claim 13, wherein the deformation of the pressure side/sides takes place by inner struts of the drive body/bodies without any additional external energy supply.

15. The conveying device in accordance with claim 1, wherein the deformation of a pressure side of the at least one drive body takes place by the so-called fin-ray effect.

16. The conveying device in accordance with claim 11, wherein the at least one drive body comprises polyurethane.

17. A conveying device for the conveying of a fluid in a conveying direction having at least one drive body which can be driven by a drive system and which has a conveying surface, wherein the drive body can be driven in an oscillating manner transversely to the conveying direction, the conveying device also having blocks which are laterally fastened to the drive body and which form a barrier between different conveying surfaces of the drive body, the drive body having a thickened upstream end and a tapered downstream, elastically deformable end, and wherein the drive body can be compressed together with a housing surrounding it.

18. The conveying device in accordance with claim 17, wherein at least one block is connected either to two drive bodies or to one drive body and the housing of the conveying device.

19. The conveying device in accordance with claim 18, wherein a driving force is applied to the drive body/bodies by the blocks.

* * * * *

UNITED STATES PATENT AND TRADEMARK OFFICE
CERTIFICATE OF CORRECTION

PATENT NO.        : 8,814,543 B2  
APPLICATION NO.   : 13/261361  
DATED             : August 26, 2014  
INVENTOR(S)       : Liebing Page 1 of 18

It is certified that error appears in the above-identified patent and that said Letters Patent is hereby corrected as shown below:

Please delete patent 8814543 in its entirety and insert patent 8814543 in its entirety as shown on the attached pages.

Signed and Sealed this
Twenty-eighth Day of April, 2015

Michelle K. Lee
*Director of the United States Patent and Trademark Office*

(12) United States Patent
Liebing

(10) Patent No.: US 8,814,543 B2
(45) Date of Patent: Aug. 26, 2014

(54) CONVEYING DEVICE FOR A FLUID USING AN OSCILLATING BODY ARRANGEMENT

(75) Inventor: Reiner Liebing, Potsdam (DE)

(73) Assignee: ECP Entwicklungsgesellschaft mbH, Berlin (DE)

( * ) Notice: Subject to any disclaimer, the term of this patent is extended or adjusted under 35 U.S.C. 154(b) by 0 days.

(21) Appl. No.: 13/261,361

(22) PCT Filed: Jan. 27, 2011

(86) PCT No.: PCT/EP2011/000439
§ 371 (c)(1),
(2), (4) Date: Oct. 3, 2012

(87) PCT Pub. No.: WO2011/092034
PCT Pub. Date: Aug. 4, 2011

(65) Prior Publication Data
US 2013/0019968 A1    Jan. 24, 2013

Related U.S. Application Data

(60) Provisional application No. 61/298,581, filed on Jan. 27, 2010.

(51) Int. Cl.
*F04D 33/00*    (2006.01)
*A61M 1/12*    (2006.01)
*A61M 1/10*    (2006.01)

(52) U.S. Cl.
CPC .......... *A61M 1/12* (2013.01); *A61M 1/101* (2013.01); *F04D 33/00* (2013.01); *A61M 1/125* (2013.01)
USPC .......................................... 417/436; 623/3.1

(58) Field of Classification Search
CPC .................................. F04D 33/00; A61M 1/12
USPC .......... 417/436; 600/16, 17, 18; 137/565.01; 623/3.1, 3.22
See application file for complete search history.

(56) References Cited

U.S. PATENT DOCUMENTS

| | | | |
|---|---|---|---|
| 2,728,298 A * | 12/1955 | Shafer | 417/343 |
| 4,063,826 A * | 12/1977 | Riepe | 417/410.1 |
| 5,820,542 A | 10/1998 | Dobak, III et al. | |
| 6,544,216 B1 | 4/2003 | Sammler et al. | |
| 6,659,740 B2 * | 12/2003 | Drevet | 417/436 |
| 6,860,713 B2 | 3/2005 | Hoover | |
| 7,393,181 B2 | 7/2008 | McBride et al. | |
| 7,874,882 B2 | 1/2011 | Sagov | |
| 7,914,436 B1 * | 3/2011 | Kung | 600/18 |
| 7,927,068 B2 | 4/2011 | McBride et al. | |
| 2006/0253193 A1 * | 11/2006 | Lichtenstein et al. | 623/3.1 |
| 2011/0034874 A1 | 2/2011 | Reitan et al. | |
| 2011/0236210 A1 | 9/2011 | McBride et al. | |
| 2011/0275884 A1 | 11/2011 | Scheckel | |
| 2011/0282128 A1 | 11/2011 | Reitan et al. | |

FOREIGN PATENT DOCUMENTS

| | | |
|---|---|---|
| DE | 103 37 804 A1 | 3/2005 |
| EP | 2 194 278 A1 | 6/2010 |

(Continued)

*Primary Examiner* — Nathan Zollinger
(74) *Attorney, Agent, or Firm* — Marshall & Melhorn, LLC

(57) ABSTRACT

The invention relates to a conveying device for conveying a fluid in a conveying direction having one or more drive bodies which can be driven in an oscillating manner by means of a drive system transversely to the conveying direction. An acceleration of the fluid is achieved by a corresponding movement in translation or by a partially pivoting movement of the drive bodies in the manner of the fin principle known from biology (e.g. aerodynamics and hydrodynamics).

19 Claims, 10 Drawing Sheets

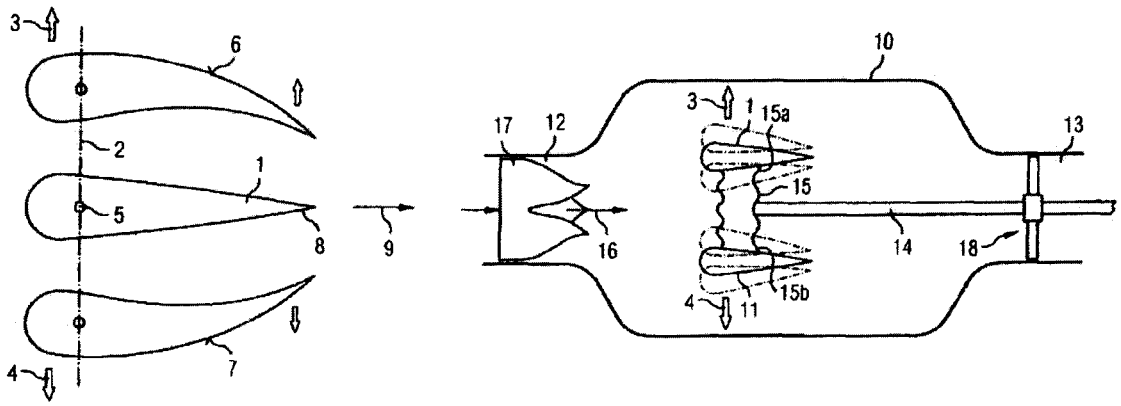

US 8,814,543 B2
Page 2

(56) References Cited

FOREIGN PATENT DOCUMENTS

| | | | |
|---|---|---|---|
| FR | 1 218 663 A | | 5/1960 |
| GB | 2041447 A | * | 9/1980 |
| WO | WO 98/18508 A1 | | 5/1998 |
| WO | WO 2005/003545 A1 | | 1/2005 |
| WO | WO 2006/038808 A1 | | 4/2006 |
| WO | WO 2009/157840 A1 | | 12/2009 |

* cited by examiner

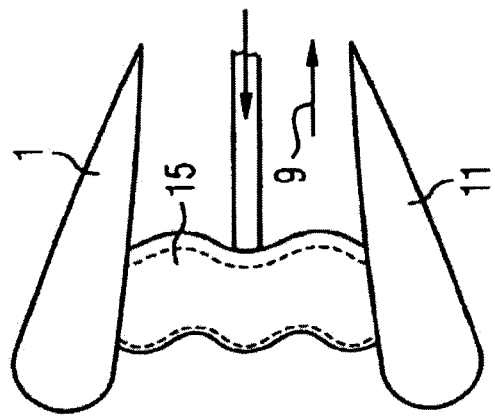
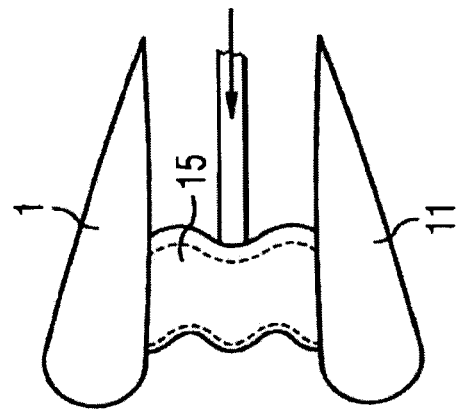
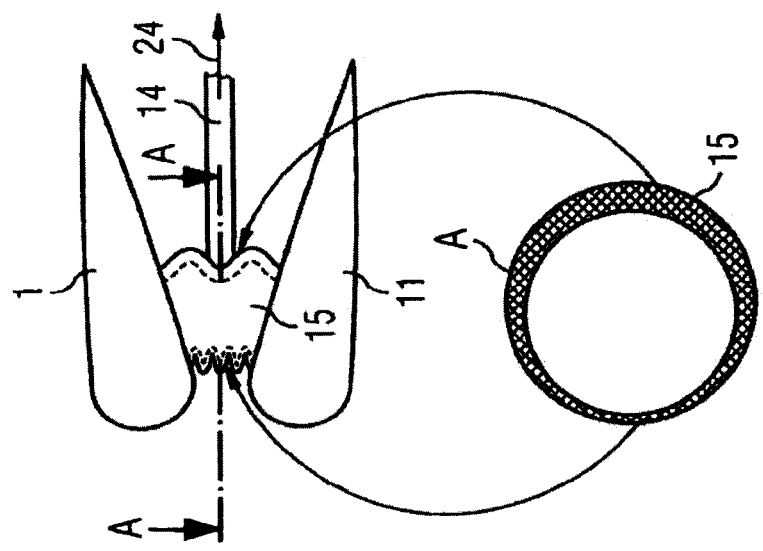

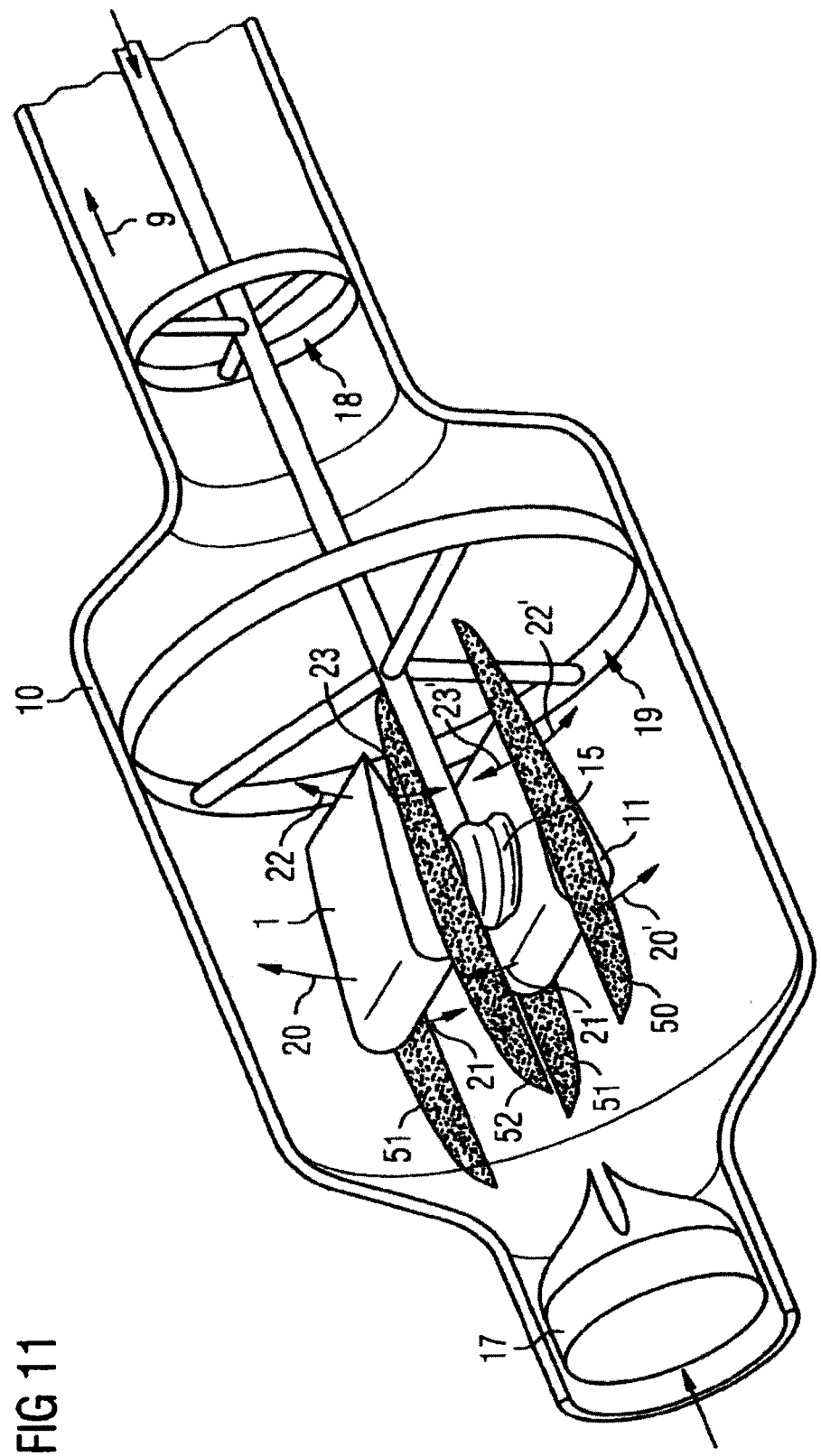

CONVEYING DEVICE FOR A FLUID USING AN OSCILLATING BODY ARRANGEMENT

BACKGROUND OF THE INVENTION

The invention is in the field of mechanical engineering and relates to conveying devices for fluids, in particular for liquids.

Such conveying devices have become known in the form of different kinds of pumps in the most varied of embodiments. Pumps are of particular interest at this point which can be manufactured in such constructions that they can be used for more sensitive fluids, in particular fluids having macromolecules. A specific group among such pumps is represented by the fluid pumps which can be used for medical application purposes and which can be manufactured in small constructions. Such pumps can also be used in micro constructions, for example, for conveying the body's own fluids, or biocompatible fluids, for example as heart pumps for conveying blood.

In the conveying of such sensitive fluids such as blood which have large and sensitive molecules, for example, which satisfy biological functions and which therefore also may not be damaged at the microscopic level, care must be taken that the mechanical effect on the fluid by pressure maxima, shear forces and accelerations is limited as much as possible.

Axial flow pumps have in particular become known in this connection, for example, for the conveying of blood which have a rotor which rotates about a longitudinal axis, which has impeller blades and which continuously conveys blood in the axial direction.

Since a specific problem for the use of such pumps in the inside of the body comprises the fact of providing them, on the one hand, with sufficient conveying capacity, and, on the other hand, however, of configuring the construction size so that they can be introduced through a blood vessel, some of the challenges for such pumps comprise the fact of configuring them from a construction aspect so that they are radially compressible and expandable again for operation in the body.

A compressible rotor of this kind is known, for example, from U.S. Pat. No. 6,860,713. Another rotor is known from U.S. Pat. No. 7,393,181 B2. In the known solutions, the rotors are compressible and expandable either due to the elasticity and deformability of the material or on the basis of mechanically movable constructions.

It is unavoidable in this respect that a certain construction effort is exerted to ensure the compressibility of such a pump despite a corresponding reliability and conveying capacity. It must moreover be ensured that large shear forces which can damage sensitive fluids do not arise due to too high a rotational speed of the rotor or due to unfavorable geometrical shapes of impeller blades. In addition, care must be taken that pressure differences within the geometry of such a conveying device, on the one hand, and over the course of time, on the other hand, are kept within tight limits.

BRIEF SUMMARY OF THE INVENTION

Under these conditions and against the background of the prior art, it is the underlying object of the present invention to provide a conveying device which can be manufactured with means which are simple from a construction aspect and which reliably and gently allow the conveying of a fluid.

The object is achieved in accordance with the invention by the features of claim 1, alternatively by the features of claim 3 or claim 7.

The conveying device in accordance with the invention, which serves to move a fluid in a conveying direction, for this purpose has a drive body which can be driven by means of a drive system and which can be driven in an oscillating manner transversely to the conveying direction.

The drive body is arranged in a channel or in a space in which the fluid should be conveyed in a preset conveying direction.

Known conveying mechanisms such as centrifugal pumps or the above-named axial flow pumps make use of rotating conveying elements for moving or accelerating a fluid. The likewise known piston pumps respectively have at least one piston which is substantially movable in translation and which conveys the medium in its direction of movement on its movement.

In contrast to this, in accordance with the present invention, the drive body is moved transversely to the conveying direction in the manner of a fin of a fish which is used in nature as a rule to generate a relative movement between the fin and a fluid. In the present invention, the fin-like element, the drive body, is in this respect substantially fixed in the conveying direction so that the relative movement results in a conveying movement of the fluid.

The movement of the drive body transversely to the conveying direction in this respect, for example, means that at least one part of the drive body is moved in translation or along a less curved path substantially perpendicular to the conveying direction and/or associated with a pivot movement about an axis which is substantially perpendicular to the conveying direction. In this respect, the deviation of the direction of extent of the axis to the perpendicular of the conveying direction should amount to a maximum of 45°. In this respect, movement patterns of fin-like bodies in fish and other creatures known from bionics should be reproduced.

The corresponding drive bodies can be adapted in shape and size to the available space. The relative movement of the drive body or of different parts of said drive body with respect to the fluid to be driven can be kept in a range with respect to the speed which prevents the creation of unpermitted shear forces. In this respect, the relative speed is to be coordinated with the viscosity of the medium to be conveyed and accordingly with possibly present compressibilities. The conveying principle described can be used particularly efficiently with substantially non-compressible and slightly liquid media such as blood. Corresponding drive movements can also be transmitted easily to a drive body to be moved in an oscillating manner. A rotatable journalling of a rotor does not necessarily have to be provided.

The drive body or bodies are flowed around by the fluid to be conveyed at multiple sides, in particular at all sides. In particular when two mutually opposite conveying surfaces are provided, they are each both in contact with the fluid to be conveyed.

The drive body or bodies are compressible together with a housing surrounding them in the radial direction with respect to the conveying direction. For this purpose, the drive bodies can be configured as foldable, as elastically compressible as foam or as inflatable. The housing can likewise be foldable and can comprise a membrane spanned over a support frame. The support frame can comprise a plastic or a metallic memory alloy, for example Nitinol or another superelastic material. The housing can also be configured as inflatable, in particular as a double-wall balloon body.

Since a certain periodicity of pressure fluctuations is to be expected due to the oscillatory movement of the drive body, with an occasional reversal of the flow direction not always being able to be precluded on such pressure fluctuations, the arrangement of a control valve for the flow to be generated in the conveying channel or in the space in which the drive body is located can also advantageously be considered. In this respect, the valve can either be controlled by an intelligent control synchronously with the movement of the drive body or it can be configured as an automatically acting check valve.

The conveying surface or a conveying surface of the drive body is advantageously aligned so that a partial force acts on the fluid in the conveying direction on a movement of the drive body. For this purpose, the direction of movement of the drive body and the direction of extent of the surfaces of the drive body at which a pressure increase arises are to be correspondingly coordinated with one another.

In this connection, at least two conveying surfaces can be provided, for example at a single drive body, which are aligned so that they each effect a conveying of the fluid in at least one of the directions of movement of the drive body. A conveying of the fluid in both drive movement directions or in a plurality of drive movement directions thus becomes possible. Two conveying surfaces can be provided at two different, mutually opposite outer surfaces of a drive body.

Provision can moreover advantageously be made that at least one drive body tapers in the conveying direction in the cross-section disposed parallel to its movement plane.

The drive body can, for example, be configured in the manner of a fin as a wedge-shaped body whose thickened end is arranged upstream with respect to the flow to be produced and whose tapered end is arranged downstream. The tapered end can converge acutely in the form of a blade edge, with the blade edge being able to extend perpendicular to the drive direction of the drive body. The drive body can also be widened toward its tapered end in the direction of extent of the cutting blade.

The conveying surfaces at both sides of such a wedge-shaped fin body can be either planar or convex or concave, viewed in the direction perpendicular to the movement plane or to the drive direction of the drive body.

The drive body can be stiff in one type of embodiment of the invention. In this case, the drive body can be pivotable about an axis which lies in the region of its thickened end. In addition, a superimposed movement in translation of the thickened end can be provided, for example in a straight manner or along a gate path. The movement portion in translation takes place in the same plane as the pivot movement in this respect.

Alternatively to this, provision can also be made that the drive body is so elastic that it can also be bent in operation in its end region by the fluid counterpressure by at least 5°, in particular also by at least 20°, with respect to the undistorted state.

The drive can in this case be configured in the same manner as with a stiff drive body, but the alignment of the conveying surfaces relative to the fluid to be conveyed in the respective phase of the drive movement can already be optimized and thus the efficiency of the drive increased by the elasticity and deformability of the drive body per se.

Such a drive body, whether stiff or elastic, can either be configured as symmetrically wedge-shaped, with planar, concave or convex conveying surfaces in the cross-section viewed perpendicular to the plane of the drive movement or a shape asymmetrical in the named cross-section can also be provided, for example with elements of an airfoil wing, to utilize additional flow effects. Such an airfoil section, for example, provides a convex shape on one side of the drive body and a convex or straight shape of the conveying surface on the opposite side.

On the use of such an asymmetrical design of a drive body, a further drive body can additionally be provided which is shaped and arranged in mirror form with respect to the first drive body and which is movably in synchronization with it in the same or opposite sense.

Provision can moreover be made to increase the efficiency of the drive that the drive body, in particular in the region of a conveying surface, has optimized surface structures.

In an advantageous embodiment of the invention, provision can moreover be made that the drive body has at least one hollow space. The provision of a hollow space reduces the mass of the drive body and thus the energy to be expended for its acceleration. In addition, the drive body can be configured as at least partially inflatable so that its outer dimensions in the non-inflated state can be smaller than in the inflated state. Such a drive body can then be brought more easily to its deployment site in the non-inflated state and inflated to the operating dimensions there. This is in particular advantageous when the conveying device should be manufactured in very small dimensions and moved within blood vessels.

The drive body can moreover advantageously comprise a foam, in particular polyurethane. The drive body can thus be manufactured as elastically deformable and as very light. The drive body can also comprise a hardenable material or generally a material whose deformability can be directly changed by physical influence, e.g. by irradiation, temperature change or by chemical reactions.

Provision can be made in the conveying device in accordance with the invention by providing a corresponding drive system that the drive body can be driven by means of a hydraulic or pneumatic device, in particular by means of a balloon body, but also by means of an electric and/or magnetic device.

Although one or more drive bodies in accordance with the invention can be moved simply by means of levers or similar mechanical devices, the drive movement can particularly easily be conducted to the conveying device by a hydraulic or pneumatic drive device. Corresponding pneumatic or hydraulic lines can be laid, for example, in the form of a hollow catheter or also within a hollow catheter, at the distal end of which the conveying device is provided, and can either act directly on a piston, bellows or balloon-like drive body in the region of the conveying device or can be converted into a lever movement there.

Possible drive movements of the drive body or bodies in this respect provide that at least one drive body is pivotable in an oscillating manner about an axis extending transversely to the conveying direction; and/or that one or more drive bodies are pivotable in an oscillating manner about an axis extending in the conveying direction, in particular outside the conveying bodies.

It is special about such an oscillatory movement that the pivot movement has a relatively small stroke so that a full rotation of the drive body does not take place in any case.

A rotation about larger angles can, however, also be provided on the rotation about an axis extending in the conveying direction.

To reduce unwanted pressure compensation procedures at the drive bodies, blocking bodies can be arranged on them between their conveying surfaces. Said blocking bodies should be flexible and can in this respect be configured as pliable or stiff, but bendable. The blocking bodies can also connect two respective blocking bodies to one another or one blocking body to a housing wall.

Provision can also be made that the driving force is transmitted to a drive body by means of a blocking body.

The described fin-like drive principle for fluids is novel in connection with the conveying of liquids and thus allows the realization of conveying characteristics which cannot be achieved with the already known conveying devices.

BRIEF DESCRIPTION OF THE DRAWINGS

Figure 14:
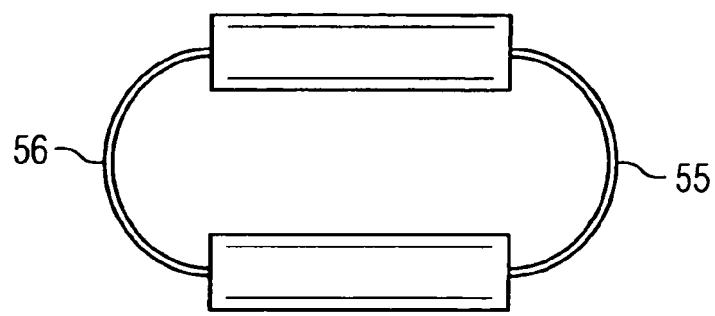
FIG. 14 the embodiment of FIG. 13 in a front view.

The invention will be shown and subsequently described in the following with reference to an embodiment in a drawing.
There are shown FIG. 1 a drive body in three positions in cross-section;

FIG. 2 a conveying system for fluids having two drive bodies in a longitudinal section;

FIG. 3 a conveying system having two drive bodies in a three-dimensional view;

FIG. 4 two drive bodies in a first position with a drive system;

FIG. 5 the drive bodies from FIG. 4 in a second position;

FIG. 6 the drive bodies from FIGS. 4 and 5 in a third position;

FIG. 7 a drive system in a three-dimensional representation having a conveying space quadrangular in cross-section;

FIG. 8 two drive bodies which are rotated in an oscillating manner about an axis extending in the conveying direction;

FIG. 9 a drive system in a three-dimensional view having two partly cylindrical drive bodies;

FIG. 10 a section through the drive system of FIG. 9;

FIG. 11 an embodiment as in FIG. 3 with additional blocking bodies;

FIG. 12 an embodiment similar to that of FIG. 7 with blocking bodies;

FIG. 13 a representation of two drive bodies which are connected by means of blocking bodies;

FIG. 14 the embodiment of FIG. 13 in a front view;

FIG. 15 a view of the embodiment of FIG. 13, with the effect of a driving force on the blocking bodies being indicated;

FIG. 16 an arrangement in which the blocking bodies have a stiff, but bendable ring-strip shape;

FIG. 17 a drive body having fin-rays in the neutral state; and

FIG. 18 a drive body as in FIG. 17 in the loaded state.

DETAILED DESCRIPTION OF THE INVENTION

FIG. 1 shows in the middle part a drive body 1 in section which substantially has a wedge shape which is modeled on the shape of a fin occurring in biology. The drive body 1 extends perpendicular to the plane of the drawing with an unchanging section, but can also widen perpendicular to the plane of the drawing toward its tapered end.

The drive body 1 can be moved in an oscillating manner along the dotted line 2 in the directions indicated by the arrows 3, 4. The region about the point of attack of the driving force is in this respect shown as a circle and is marked by 5. The driving force engages at this point such that the drive body is moved substantially in translation along the line 2 and is thus not pivotable in a first variant to avoid an active fluid counterpressure.

A fluid counterpressure then results in operation, for example on the movement of the drive body within a liquid, on the side of the respectively acting conveying surface 6, 7, said fluid counterpressure resulting in a deformation of the end 8 of the drive body 1 remote from the drive, i.e. the tapered end, when this drive body is configured as elastic as in the example shown. A particularly efficient advance of the driven fluid in the conveying direction 9 results by this effect.

Alternatively, the drive of the drive body 1 can also be configured so that it is not driven strictly in translation in the sense of the directions 3, 4, but rather in a superimposed movement in translation and in a pivot movement. In this respect, for example simultaneously with the movement in the direction of the arrow 3, a pivoting of the drive body takes place about the point of attack 5 clockwise about a specific angle, for example 10°, so that the drive body inclines at the end of the movement in a similar manner as under the effect of a fluid counterpressure. Optionally, the direction of rotation of the pivot movement can be reversed at the end of the movement in translation to beat with the fin. This driving principle can be combined both with stiff drive bodies and with flexible drive bodies.

A specific lever drive or a gate drive of the drive body can be provided for this purpose or it is conceivable to transmit the driving forces by means of a hydraulic or pneumatic apparatus.

FIG. 2 shows in a side view a housing 10 in which a conveying device in accordance with the invention having two drive bodies 1, 11 is arranged. The housing 10 is set up rotationally symmetrically or elliptically in cross-section about the drive bodies 1, 11 and has an inflow channel 12 as well as an outflow channel 13. A fluid line 14 which is part of the drive system and which is connected to a drive bellows 15 projects through the outflow channel 13. The drive bellows 15 can be connected via a pressure control device, not shown, via the fluid line 14 to an overpressure or to an underpressure so that said drive bellows can be inflated or deflated by the inflow of a fluid or the removal of the fluid.

One respective drive body 1, 11 is fastened to the two ends 15a, 15b of the drive bellows 15 and runs through a drive movement in the direction of the arrows 3, 4 by the volume changes of the drive bellows. The drive movement in translation of the drive bellows 15 can be translated into a more complex movement path of the drive bodies 1, 11, which can correspond to a superimposition of the movement in translation with a pivot movement, by a corresponding elastic configuration of the drive bellows 15 or by additional levers which connect the bellows to the drive bodies 1, 11 or the drive bodies to a fixed point of the housing 10.

Provision can, however, also be made that the movement of the drive bodies 1, 11 substantially takes place in translation and said drive bodies are configured as elastic to carry out the elastically fin-like overall movement shown with reference to FIG. 1.

If the pressure in the drive bellows 15 is changed periodically via the control of the fluid pressure in the fluid line 14, for example several times per second, this is translated into an oscillatory movement of the drive bodies 1, 11. This results in an acceleration of the fluid located in the housing 10 in the direction of the arrow 16 which designates the conveying direction of the fluid. Since pressure fluctuations occur due to the periodicity of the movement, it may be meaningful to provide a check valve 17 in the inflow channel 12 which blocks the inflow channel 12 for the case that an overpressure arises within the housing 10 in front of the valve and closes it again as soon as an underpressure is generated there.

The fluid line 14 can be configured as a flexible hose line provided that the drive bellows 15 is held otherwise in the housing 10. The drive line 14 can, however, also be configured as a rigid line in the form of a pipe in order simultaneously to conduct the fluid and to fix the drive bellows and the drive bodies 1, 11. The fluid line 14 can in every case be held and fixed in a holding star 18 or at a holding arm within the outflow channel 13.

In the Figure, three positions are shown for each drive body 1, 11, with a middle neutral position being shown by solid lines and the extreme positions on the movement path of each individual drive body 1, 11 being shown by broken lines.

FIG. 3 shows a similar arrangement to FIG. 2, but in a three-dimensional view, with a second holding star 19 being provided in addition to the first holding star 18 in direct vicinity of the drive bellows 15 and of the drive bodies 1, 11.

Arrows 20, 21 and 20', 21' are drawn in which indicate the directions of movement of the respective thickened ends of the drive bodies 1, 11 as are arrows 22, 23 and 22', 23' which indicate the movement of the tapered ends of the drive bodies 1, 11. The different lengths of the arrows shown should indicate that the thickened ends of the drive bodies 1, 11 facing the one-way valve 17 carry out a pivot movement whose amplitude is substantially larger than the movement of the tapered ends of the drive bodies. This is made possible, as will be shown in more detail with reference to FIGS. 4, 5 and 6, by a special construction of the drive bellows 15.

FIG. 4 shows in a side view in the upper part the two drive bodies 1, 11 as well as the drive bellows 15 in the deflated, i.e. compressed, form. The arrow 24 indicates that an underpressure is present in the fluid line 14 in this state to compress the drive bellows 15.

The drive bellows 15 itself has an asymmetrical structure, as can be seen more clearly from the lower part of FIG. 4. A cross-section through the drive bellows 15 along the dashed line A is shown there which makes clear that the drive bellows has a smaller wall thickness in its region facing the one-way valve 17 than in the outflow channel 13.

It is thereby achieved that the movement amplitude is larger in the front region facing the inflow channel 12 than in the rear region of the drive bellows facing the outflow channel 13. A pivot movement of the drive bodies 1, 11 therefore results on a pressure change in the drive bellows 15.

In FIG. 5, the arrangement of FIG. 4 with the drive bodies 1, 11 and a drive bellows 15 inflated further with respect to FIG. 4 is shown. The drive bodies are approximately in the straight position shown in FIG. 2.

FIG. 6 finally shows the state of the drive bodies 1, 11 in the fully inflated state of the drive bellows 15, with it also becoming clear that the thickened ends of the drive bodies 1, 11 have passed through a larger movement amplitude than the tapered ends so that a pivot movement of the drive bodies has taken place in addition to a movement in translation.

FIG. 7 shows in a three-dimensional view from a different perspective two drive bodies 1', 11' which are configured as asymmetrical in the manner of an aerodynamic airfoil section, but which may additionally also be configured as flexible and which can be driven by means of a drive bellows 15. The inflow channel 12 is shown in the foreground of the figure, the outflow channel 13 in the background. In contrast to the cylindrical housing 10 of the arrangement shown in FIG. 3, the housing 10' shown in FIG. 7 has a parallelepiped structure with a rectangular cross-section to implement the non-cylindrically symmetrical structure of the drive arrangement and of the drive bodies as efficiently as possible. Unlike the specific representation of FIG. 7, the transition from the housing 10' to the inflow and outflow channels 12, 13 can take place with conical or oblique transitions. Provision can advantageously be made that the drive bodies 1', 11' extend perpendicular to the plane of the drive movement up to as close as possible to the side walls 25, 26 of the housing 10'. Turbulence at the side surfaces of the drive bodies 1', 11' is thereby reduced.

The drive bodies 1', 11' can, just like the drive bodies 1, 11 shown further above, comprise a foam, in particular polyurethane, and can be inflatable. For this purpose, the bodies can have large and/or a plurality of small hollow spaces which can, for example, be inflated by the drive fluid via the fluid line 14 and which have check valves to be stabilized in the inflated state.

A good compressibility in the non-inflated state is hereby made possible so that the drive bodies can be radially compressed for transport to a deployment site together with the housing 10, 10' and can be expanded on site before they are put into operation.

FIG. 8 shows an arrangement in comparison with the Figures described further above having two drive bodies 1", 11" with another drive principle in which the drive bodies are connected via connection webs 28, 29 to a drive shaft 27 which extends in the conveying direction 30.

The drive shaft 27 can be rotated in an oscillating manner about the conveying direction 30, and indeed in each case, for example, at least by an amount of 5°, 10° or at least by 20° or 30°, in each direction, as indicated by the arrows 33, 34.

The longitudinal axes of the drive bodies 1" and 11" are aligned parallel to the shaft and undergo a movement quasi in translation in the peripheral direction of the shaft in the directions which are indicated by the arrows 31, 32 within the framework of this rotary movement, provided that the length of the connection webs 28, 29 is sufficient. In this manner, a corresponding approximately linear movement in translation of the drive bodies can be realized in a very simple manner by means of the drive shaft 27. In FIG. 8, a plurality of parallel microgrooves 41 are also shown by way of example at the lower drive body 11".

In FIG. 9, an arrangement is shown in a three-dimensional view which is as largely cylindrically symmetrical as possible of two drive bodies 1''' and 11''' which are connected by a drive bellows 15' and which can be moved substantially in the direction of the arrows 35, 36 in the radial direction with respect to the cylinder axis. The drive bellows 15' is connected to a pressure generation system by means of a fluid line 14. It is also conceivable to divide the cylindrically symmetrical arrangement into a higher number of cylinder segments, for example 4 or 8 or more and to move them radially in each case, with a movement pattern resulting which is similar to the manner of propagation of jellyfish.

A section through the arrangement of FIG. 9 is shown in FIG. 10 which makes the function clear. The drive body 1''' is shown by way of example with a hollow space 37, the drive body 11''' with a hollow space 38, with the hollow spaces only being indicated schematically.

Fluid is exchanged via the fluid line 14 with the interior of the drive bellows 15 and is pumped from there into the hollow spaces 37, 38, with the hollow spaces 37, 38 of the drive bodies 1''' and 11''' being connected to the hollow space of the drive bellows 15' by means of one-way valves 39, 40 so that the drive bodies are only inflated once and then thereafter maintain the increased fluid pressure to be stabilized in shape. Only the interior of the drive bellows 15' is inflated and deflated thereafter. The drive bodies 1''', 11''' thereby alternately move apart in the direction of the arrows 35, 36 and move together in the opposite direction, whereby a corresponding drive movement is realized.

The efficiency of the conveying device with respect to the non-cylindrically symmetrical arrangements which are shown in the aforesaid Figures is increased by the cylindrically symmetrical or approximately cylindrically symmetrical arrangement of the drive bodies.

FIG. 11 shows a cylindrical arrangement of a housing 10 having two drive bodies 11 which are each laterally provided with blocking bodies 50, 51, 52, 52 which are flexible and may also be connected to the wall of the housing 10 and which prevent or reduce a pressure equalization between the lower side and upper side or the high pressure side and low pressure side of each drive body during the drive movement.

FIG. 12 shows corresponding blocking bodies 53, 54 for a housing 10' with flattened side walls.

FIG. 13 shows two blocking bodies in the form of wide, flexible bands 55, 56 which connect two drive bodies to one another at both sides. This constellation is shown in a front view in FIG. 14.

FIG. 15 shows two blocking bodies 55, 56, as in FIG. 13, which connect two fin-like drive bodies to one another and act as an equalization block. The blocking bodies are configured as strips and can be configured as flexible or stiff and elastically pliable. In the latter case, a drive movement can be directly applied to the drive bodies by direct application of a mechanically, magnetically, pneumatically hydraulically or electrically generated driving force onto the blocking bodies from the outside, indicated by the arrows $F_1$ and $F_1'$ or from the inside from the intermediate space of the drive bodies, indicated by the double arrow $F_2$.

Instead of the blocking bodies, similarly positioned coupling bodies in the form of a scaffold or frame can be provided to couple the drive movement into the sections.

The principle of the drive via the blocking bodies is additionally illustrated by way of example by FIG. 16. Two drive bodies 57, 58 are connected to one another there by two ring segments 59, 60 of a ring strip in the form of a circular ring. The cylinders 61, 62 symbolically indicate outwardly engaging driving forces which can apply a traction force or a compression force to the ring segments from the outside. Corresponding inwardly engaging forces are symbolically designated by 63, 64. A deformation of the ring segments effects a drive movement of the drive bodies 57, 58. They can be controlled in a suitable manner by a profiling of the ring segments 59, 60 or by cut-outs in the ring segments.

In FIGS. 17 and 18, a drive body is shown in a schematic plan view having so-called fin-rays 65 which have an influence on the flow of the fluid on the surface as web-like, groove-like or fin-like structures. They can be shaped and configured by their inner structure such that they effect a concave deformation and thus an increase in pressure on the pressure side on a movement of the drive body. This deformation against the pressure takes place automatically without any additional external energy supply and thus substantially differs from the deformation of customary beam structures which usually yield to a pressure increase on one side and evade the higher pressure.

The inner structure is formed by struts which preferably extend in the interior of a drive body from a drive surface to an oppositely disposed drive surface. The struts can in this respect be made as bars or also as plates, ribs or equivalent structures.

The conveying device for fluids in accordance with the invention allows an efficient configuration thanks to the use of an oscillatory movement transversely to the conveying direction of drive bodies, with the disadvantages of only rotating drive devices being avoided.

The invention claimed is:

1. A conveying device for the conveying of blood in a conveying direction having at least one drive body which can be driven by a drive system and which has a conveying surface, the drive body having a thickened upstream end and a tapered downstream, elastically deformable end, wherein the drive body can be driven in an oscillating, fin-like manner transversely to the conveying direction and is flowed around on a plurality of sides by blood to be conveyed, and wherein the drive body can be compressed together with a housing surrounding it.

2. The conveying device in accordance with claim 1, wherein the drive body/bodies can be driven by a rotatable shaft.

3. The conveying device in accordance with claim 1, wherein the at least one drive body is pivotable in an oscillating manner about an axis extending transversely to the conveying direction.

4. The conveying device in accordance with claim 1, wherein the conveying surface of the at least one drive body is aligned such that a partial force acts on the blood in the conveying direction on movement of the at least one drive body.

5. The conveying device in accordance with claim 4, wherein two conveying surfaces are aligned such that they effect a conveying of the blood in a respective movement direction of the at least one drive body.

6. The conveying device in accordance with claim 1, wherein the at least one drive body tapers in the conveying direction in the cross-section disposed parallel to its movement plane.

7. The conveying device in accordance with claim 1, wherein the at least one drive body is configured as stiff.

8. The conveying device in accordance with claim 1, wherein the at least one drive body is configured as elastic such that it is bendable in its end region by the fluid counterpressure in operation by at least 5° with respect to the non-deformed state.

9. The conveying device in accordance with claim 8, wherein the at least one drive body has microgrooves extending in the conveying direction.

10. The conveying device in accordance with claim 1, wherein the at least one drive body has at least one hollow space.

11. The conveying device in accordance with claim 1, wherein the at least one drive body comprises a foam.

12. The conveying device in accordance with claim 11, wherein the at least one drive body is at least partly inflatable.

13. The conveying device in accordance with claim 1, wherein the drive body/bodies is/are deformed in operation against the fluid pressure on the respective pressure side/sides.

14. The conveying device in accordance with claim 13, wherein the deformation of the pressure side/sides takes place by inner struts of the drive body/bodies without any additional external energy supply.

15. The conveying device in accordance with claim 1, wherein the deformation of a pressure side of the at least one drive body takes place by the so-called fin-ray effect.

16. The conveying device in accordance with claim 11, wherein the at least one drive body comprises polyurethane.

17. A conveying device for the conveying of a fluid in a conveying direction having at least one drive body which can be driven by a drive system and which has a conveying surface, wherein the drive body can be driven in an oscillating manner transversely to the conveying direction, the conveying device also having blocks which are laterally fastened to the drive body and which form a barrier between different conveying surfaces of the drive body, the drive body having a thickened upstream end and a tapered downstream, elastically deformable end, and wherein the drive body can be compressed together with a housing surrounding it.

18. The conveying device in accordance with claim 17, wherein at least one block is connected either to two drive bodies or to one drive body and the housing of the conveying device.

19. The conveying device in accordance with claim 18, wherein a driving force is applied to the drive body/bodies by the blocks.

* * * * *